United States Patent
Hasegawa et al.

(10) Patent No.: US 7,908,935 B2
(45) Date of Patent: Mar. 22, 2011

(54) FECES COLLECTION CONTAINER

(75) Inventors: Mitsuru Hasegawa, Osaka (JP);
Yoshikatsu Tomita, Osaka (JP); Seiji Okamoto, Osaka (JP)

(73) Assignee: Nipro Corporation, Osaka (JP)

( * ) Notice: Subject to any disclaimer, the term of this patent is extended or adjusted under 35 U.S.C. 154(b) by 375 days.

(21) Appl. No.: 12/097,467

(22) PCT Filed: Dec. 15, 2006

(86) PCT No.: PCT/JP2006/325072
§ 371 (c)(1),
(2), (4) Date: Jun. 13, 2008

(87) PCT Pub. No.: WO2007/069731
PCT Pub. Date: Jun. 21, 2007

(65) Prior Publication Data
US 2010/0000341 A1   Jan. 7, 2010

(30) Foreign Application Priority Data

Dec. 16, 2005 (JP) ................................. 2005-364129
May 16, 2006 (JP) ................................. 2006-136515

(51) Int. Cl.
*G01N 1/08* (2006.01)
*G01N 1/12* (2006.01)

(52) U.S. Cl. .................................. 73/864.64; 73/864.44

(58) Field of Classification Search .................... 73/864, 73/864.44, 864.51, 864.63, 864.64, 864.91; 600/572–573, 576, 579
See application file for complete search history.

(56) References Cited

U.S. PATENT DOCUMENTS

| 4,492,124 A | 1/1985 | Fleisher et al. |
| 5,384,097 A | 1/1995 | Brouwer |
| 5,514,341 A * | 5/1996 | Urata et al. ................... 422/102 |

FOREIGN PATENT DOCUMENTS

| EP | 727653 A2 * | 8/1996 |
| EP | 1371964 A1 * | 12/2003 |
| JP | 02-063456 U | 5/1990 |
| JP | 06-186227 A | 7/1994 |
| JP | 06-201684 A | 7/1994 |
| JP | 06-207935 A | 7/1994 |
| JP | 07092162 A * | 4/1995 |
| JP | 07-234213 A | 9/1995 |
| JP | 07333217 A * | 12/1995 |
| JP | 07333218 A * | 12/1995 |
| JP | 08-292189 A | 11/1996 |
| JP | 10-170510 A | 6/1998 |
| JP | 11-295194 A | 10/1999 |
| JP | 11-316222 A | 11/1999 |
| JP | 2004004014 A * | 1/2004 |
| JP | 2004286705 A * | 10/2004 |
| JP | 2004-317481 A | 11/2004 |

* cited by examiner

Primary Examiner — Thomas P Noland
(74) Attorney, Agent, or Firm — Sughrue Mion, PLLC

(57) ABSTRACT

The inventors perfected the present invention upon finding that a conventional fecal sampling stick is given a hollow structure that has openings a certain distant apart, permitting in aspiration through the capillary tube phenomenon. That is, the present invention is a feces collection container for collecting faeces as an analyte, which comprises a fecal sampling stick which has a holding part (11) at a base, a fecal sampling part (12) at a tip and is formed a hollow passage with openings at the tip and on the base side a predetermined distance from the tip.

14 Claims, 21 Drawing Sheets

Fig. 11
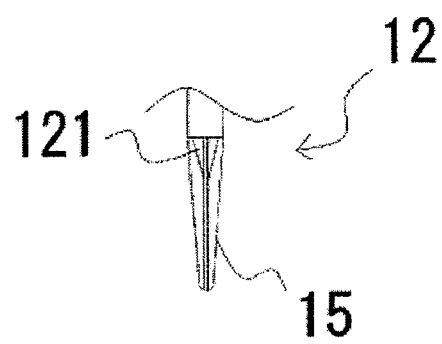
(a)
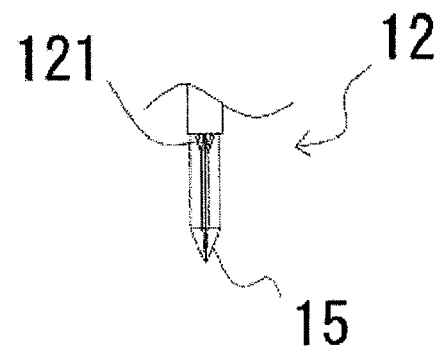
(b)
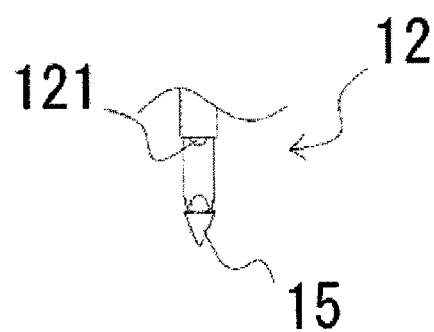
(c)

FECES COLLECTION CONTAINER

CROSS REFERENCE TO RELATED APPLICATIONS

This application is a National Stage of International Application No. PCT/JP2006/325072 filed on Dec. 15, 2006, claiming priority based on Japanese Patent Application Nos. 2005-364129 filed on Dec. 16, 2005, and 2006-136515 filed on May 16, 2006, the contents of all of which are incorporated herein by reference in their entirety.

TECHNICAL FIELD

The present invention relates to a feces collection container that is convenient for collecting fecal samples used for clinical laboratory tests, particularly occult blood, enzymes, viruses, and the like, and for transporting certain quantities while suspended in stool-dissolving buffer in the container.

BACKGROUND ART

The fecal occult blood test is widely used to screen for colon cancer or rectal cancer. Specimens are typically prepared at a hospital from a stool sample collected at home and tested. In qualitative analysis using latex, a specified fecal sampling stick is used because the amount of stool is limited when preparing the specimen, but it is difficult to obtain the proper amount of fecal sample even when using the fecal sampling stick, and in the past, the fecal sampling stick has been wiped with paper or the like to remove the excess stool after the fecal sample has been obtained.

However, stool is dirty and has a powerful odor, and may accidentally adhere to the hands or the like when wiped off with paper or the like. Another problem is that personnel preparing the specimen are often exposed to the foul odor when opening the cap of the specimen container to obtain the sample using the fecal sampling stick. After providing a fecal sample, some subjects such as elderly individuals in particular may attempt to, but do not fully, close the lid of conventional specimen containers, which contain buffer for dissolving the stool, and the containers sometimes leak during transportation.

A fecal sampling container disclosed in Japanese Laid-Open Utility Model Application 2-14068 was therefore proposed as a solution to the various problems noted above. This fecal sampling container is characterized in that an elongated container body with a drip portion at the tip is sealed with a lid that has a stick attached to it, a rubber stopper with a hole through which the stick is inserted is secured inside the container body, the space between the lid and container body is sealed with an O-ring, and a Moltopren and a filter are provided in the drip portion, wherein the stick is inserted through the insertion hole of the rubber stopper to wipe off excess stool adhering to the stick. However, drawbacks of this fecal sampling container are: the costs associated with the container are higher because the rubber stopper is expensive and the trouble must be taken to secure the rubber stopper inside the container body; the seal in the drop portion must be perforated with a perforating device when drops of the fecal suspension are to be poured out, which is cumbersome and may soil the hands; and the perforating device must be cleaned every time it is used.

As an effort to overcome the drawbacks of the fecal sampling container in the above Japanese Laid-Open Utility Model Application 2-14068, Japanese Laid-Open Patent Application H6-186227 discloses a fecal sampling container composed of a container body containing a fluid, a lid equipped with a fecal sampling stick, and a drip portion, wherein excess fecal sample on the stick can be wiped off by a separation wall provided in the top of the container body, and a thin-walled end surface at the distal end of the drop portion is perforated so that fecal sample dissolved in the liquid can be filtered by a filter provided in the bottom of the container body and quantitatively poured out in the form of drops, and Japanese Laid-Open Patent Application H8-292189 discloses a fecal sampling container composed of a liquid-holding container body that is sealed off by an intermediate member in the form of a thin film, sample collecting means, and a cap member for sealing the bottom of the container body, wherein excess fecal sample on the sample collecting means can be wiped off when the thin film is burst by the sample collection portion of the sample collecting means, and the sealing portion of the nozzle provided on the cap member is removed so that the specimen filtrate can be quantitatively poured out in the form of drops onto an assay chromatograph. Japanese Laid-Open Patent Application H11-316222 also proposes a feces collection container that has good detection accuracy and reproducibility, without the risk of viral or bacterial contamination.

Although these fecal sampling containers are all suitable for collecting solid stool, they are not suitable for collecting stool in the form of liquid diarrhea, and there is a need for a fecal sampling container that would be suitable for detecting bacteria, particularly in patients who are afflicted with diarrhea as a result of bacterial infection.

Because the tips of the sampling sticks in contact with stool in these fecal sampling containers are exposed, there is also the risk that the operator's hands or the surroundings may become contaminated until the fecal sample is suspended in the suspension after being collected. The fecal sampling stick in contact with stool may also accidentally cause stool to adhere to the outer wall of the container when inserted into the container holding the suspension, and therefore causes more problems, is unsanitary, and poses the risk of viral or bacterial contamination.

Patent Citation 1: Japanese Laid-Open Patent Application H6-186227
Patent Citation 2: Japanese Laid-Open Patent Application H8-292189
Patent Citation 3: Japanese Laid-Open Patent Application H11-316222
Patent Citation 4: Japanese Laid-Open Utility Model Application H2-140468

DISCLOSURE OF THE INVENTION

Problems to be Solved by the Invention

In view of the foregoing, an object of the invention is to provide a feces collection container that is less expensive than conventional containers, has good detecting accuracy and reproducibility, and is suitable for collecting stool in the form of liquid diarrhea in particular. Also, an object of the invention is to provide a feces collection container that there is not a risk of viral or bacterial contamination.

Means for Solving the Problems

As a result of extensive research to overcome the above problems, the inventors perfected the present invention upon finding that a conventional fecal sampling stick is given a hollow structure that has openings a certain distant apart, permitting in aspiration through the capillary tube phenomenon.

That is, the present invention is a feces collection container for collecting faeces as an analyte, which comprises a fecal sampling stick which has a holding part at a base, a fecal sampling part (12) at a tip and is formed a hollow passage with openings at the tip and on the base side a predetermined distance from the tip.

Also, it comprises fecal sampling stick, a cylindrical member being open at both ends so that the fecal sampling stick is retractably inserted, and a container body in which the tip is provided with a drip portion that is sealed off by readily openable sealing means, an outer wall of the fecal sampling stick and an inner wall of the cylindrical member are engaged in a liquid-tight manner, and the tip of the cylindrical member and the base of the container body are engaged in a liquid-tight manner. Further, the tip of the cylindrical member is sealed off by a sealing film that is penetratable by the fecal sampling stick. Moreover, the base of the container body is sealed off by a sealing film that is penetratable by the fecal sampling stick. Further more, a tip of the fecal sampling stick has a protrusion for penetrating the sealing film. Still further, the sealing means of the drip portion is a thin film that is easily breakable. In addition, the sealing means of the drip portion is a seal that is easily breakable at a fragile part. Further, the sealing means of the drip portion is a cap.

The inventors perfected the present invention upon finding that a fecal sampling stick is given a hollow structure that has openings a certain distant apart, and a base side opening is openable and closable, permitting in aspiration through the capillary tube phenomenon and preventing concentration error.

That is, the present invention is a feces collection container for collecting faeces as an analyte, which comprises a fecal sampling stick which has a holding part at a base, a fecal sampling part at a tip and is formed a hollow passage with a tip opening and a base side opening on the base side a predetermined distance from the tip, and an opening closing means which is closable to the base side opening in a liquid-tight manner.

Also, the fecal sampling stick is composed of a fecal sampling part side member and a holding part side member which are relatively displaceably connected, one of the fecal sampling part side member and the holding part side member has the base side opening, and the other that is relatively displaced from the position where the base side opening is open to the position where it is closed has the opening closing means.

Further, the fecal sampling part side member has the base side opening, and the tip of the holding part side member is the opening closing means. Alternatively, the holding part side member has the base side opening, and the base of the fecal sampling part side member is the opening closing means.

Moreover, the fecal sampling part side member and the holding part side member is slidably relatively displaceable. Alternatively, the fecal sampling part side member and the holding part side member is rotatably relatively displaceable.

Further more, it comprises the fecal sampling stick, a cylindrical member being open at both ends so that the fecal sampling stick is retractably inserted, and a container body in which the tip is provided with a drip portion that is sealed off by readily openable sealing means, an outer wall of the fecal sampling stick and an inner wall of the cylindrical member are engaged in a liquid-tight manner, and the tip of the cylindrical member and the base of the container body are engaged in a liquid-tight manner. Also, the tip of the cylindrical member is sealed off by a sealing film that is penetratable by the fecal sampling stick. Further, the base of the container body is sealed off by a sealing film that is penetratable by the fecal sampling stick. Moreover, a tip of the fecal sampling stick has a protrusion for penetrating the sealing film. Still further, the sealing means of the drip portion is a thin film that is easily breakable. In addition, the sealing means of the drip portion is a seal that is easily breakable at a fragile part. Moreover, the sealing means of the drip portion is a cap.

In addition, the opening closing means relatively displaces from the position where the base side opening is open to the position where it is closed by the resistance during the penetration of the sealing film by the fecal sampling stick.

EFFECT OF THE INVENTION

According to the above structure, the feces collection container of the invention is convenient because the container can be used to collect stool ranging from solids to liquid diarrhea using only one type of feces collection container. Bacteria that have conventionally been difficult to detect in the past can also be detected by collecting diarrhea from patients afflicted with diarrhea as a result of bacterial infection. Furthermore, because the fecal sampling stick is advanced into and retracted from a cylindrical member, allowing the fecal sampling portion to be exposed from or housed in the cylindrical member, after the fecal sample has been obtained the fecal sampling portion is housed in the cylindrical member until the cylindrical member it attached to the container body, thereby avoiding contamination by fecal matter. In addition, because the fecal sampling portion of the fecal sampling stick is inserted through the sealing film of the container body into the container, the excess fecal matter that has been obtained is removed and the predetermined amount of fecal matter is collected in the container body while the fecal sampling portion is inserted through the sealing film.

Also proposed is a feces collection container wherein the fecal sampling stick is given a hollow structure that is open at the tip and at the base at a certain interval apart, permitting in aspiration through the capillary tube phenomenon. This is suitable for collecting liquid diarrhea samples, ensuring the necessary amount of sample.

In this type of feces collection container, the internal pressure of the buffer for dissolving the stool results in positive pressure according to the volume of the fecal sampling portion, without the risk of any stool leaking backward out of the opening at the base and accidentally leading to an excessive dissolving concentration.

BRIEF DESCRIPTION OF THE DRAWINGS

FIG. 11 is a side view of the protrusion of the fecal sampling stick of the feces collection container of the invention.

Figure 1:
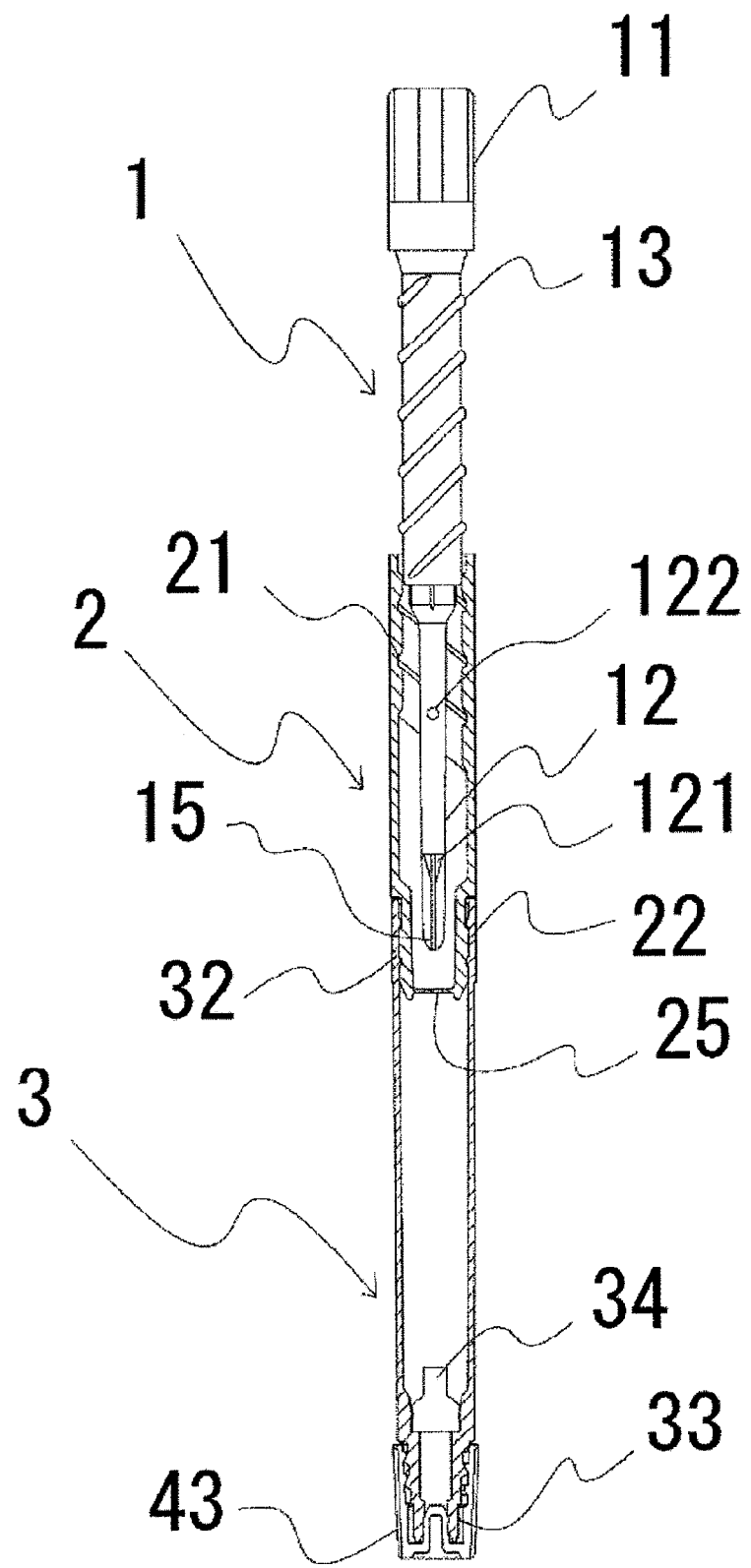
FIG. 1 is a longitudinal cross section depicting a first example of the feces collection container of the invention.

LEGENDS 1 fecal sampling stick
11 holding part
12 fecal sampling part
121 aspiration hole
122 hole for adjusting the aspiration level
13 male threading
131 protrusion
15 protrusion
2 cylindrical member
21 female threading
22 engagement member
23 ring-shaped protrusion
24 female threading
25 sealing film
3 container body
31 sealing film (opening closing means)
32 engagement member
33 drip portion
34 filter
41 film
42 seal
421 fragile part
43 cap

BEST MODE FOR CARRYING OUT THE INVENTION

Figure 2:
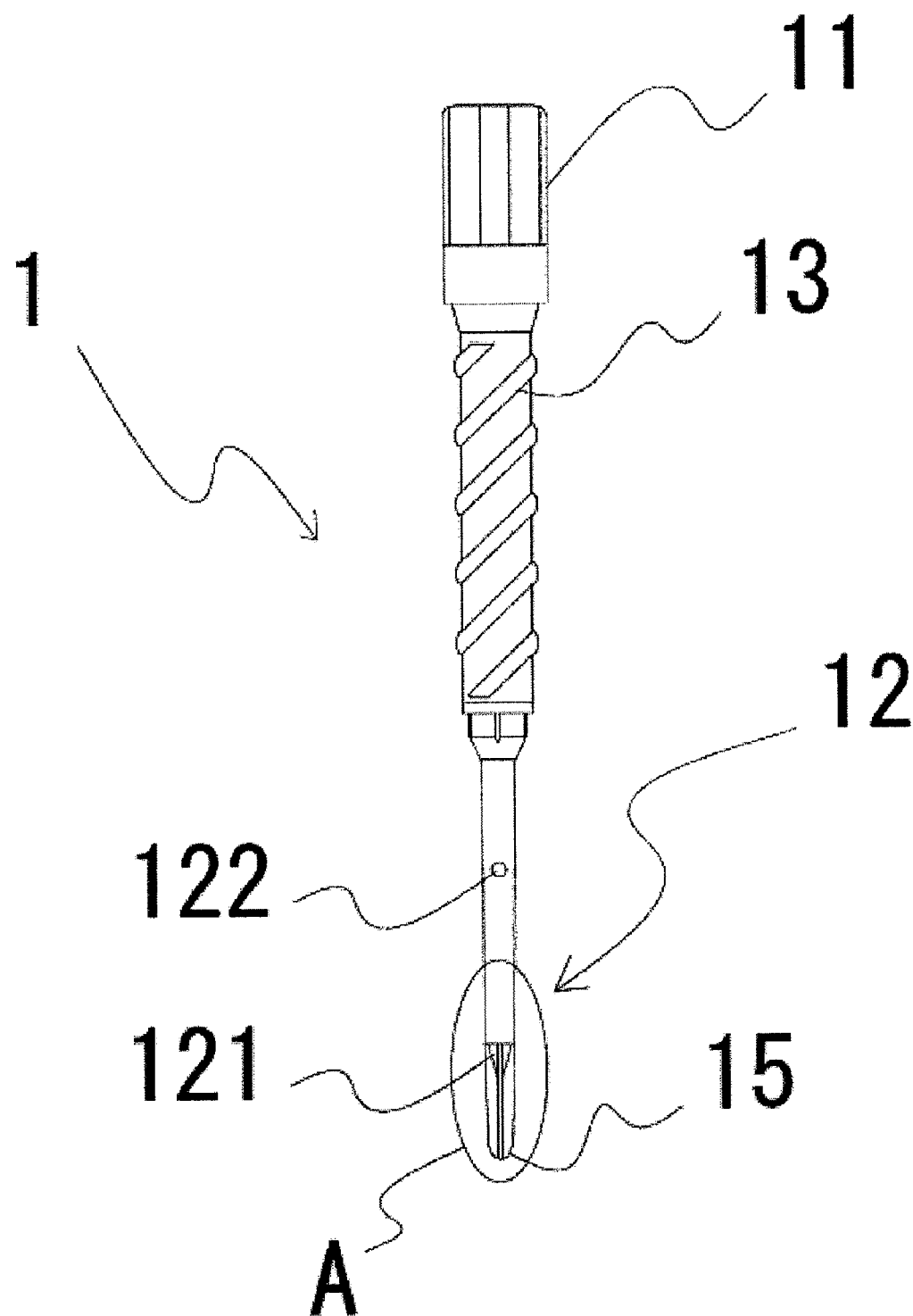
FIG. 2 is a side view of the fecal sampling stick shown in FIG. 1.
Figure 3:
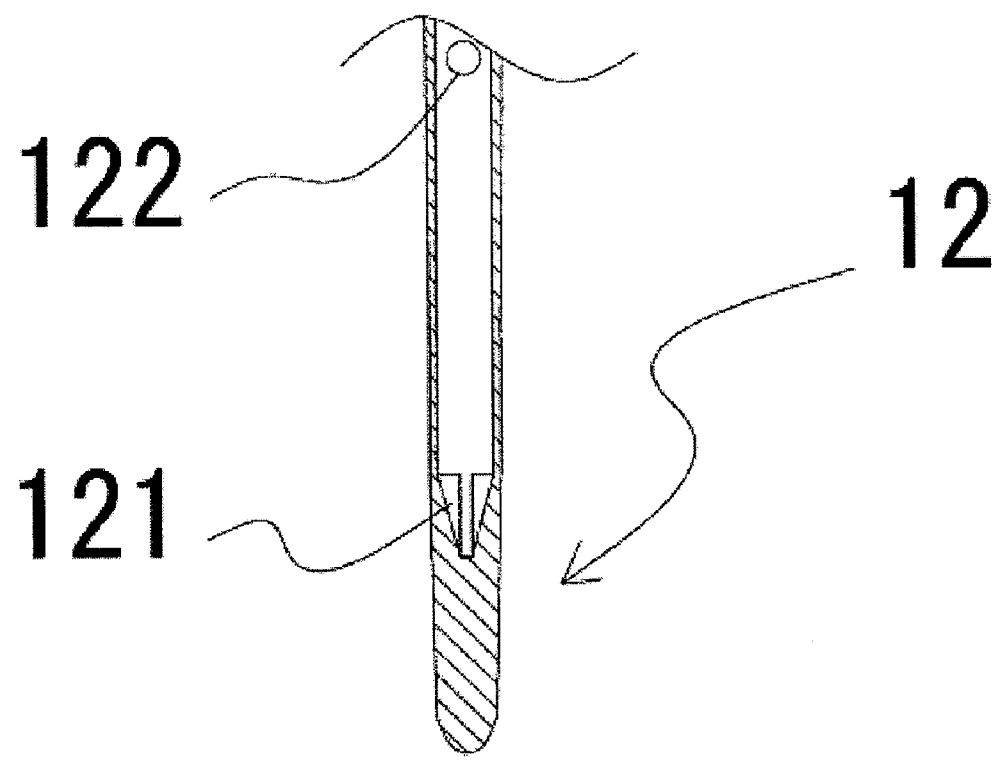
FIG. 3 is a cross sectional detail of portion A in FIG. 2.
Figure 4:
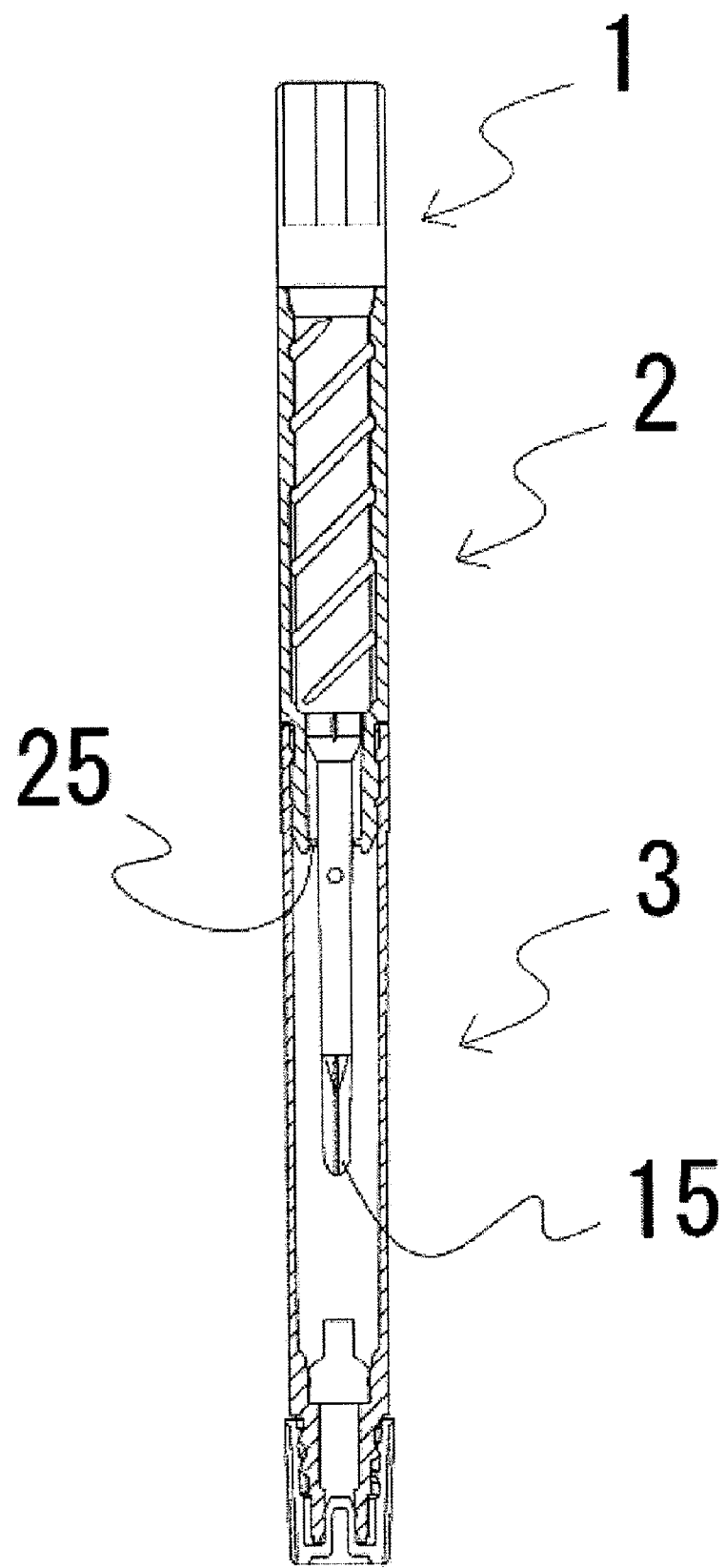
FIG. 4 is a longitudinal cross section of the sealing film penetrated by the fecal sampling stick in the feces collection container illustrated in FIG. 1.

The feces collection container of the invention is illustrated in greater detail by the figures. FIG. 1 is a longitudinal cross section depicting a first example of the feces collection container of the invention. FIG. 2 is a side view of the fecal sampling stick shown in FIG. 1. FIG. 3 is a cross sectional detail of portion A in FIG. 2. FIG. 4 is a longitudinal cross section of the sealing film penetrated by the fecal sampling stick in the feces collection container illustrated in FIG. 1.

Figure 5:
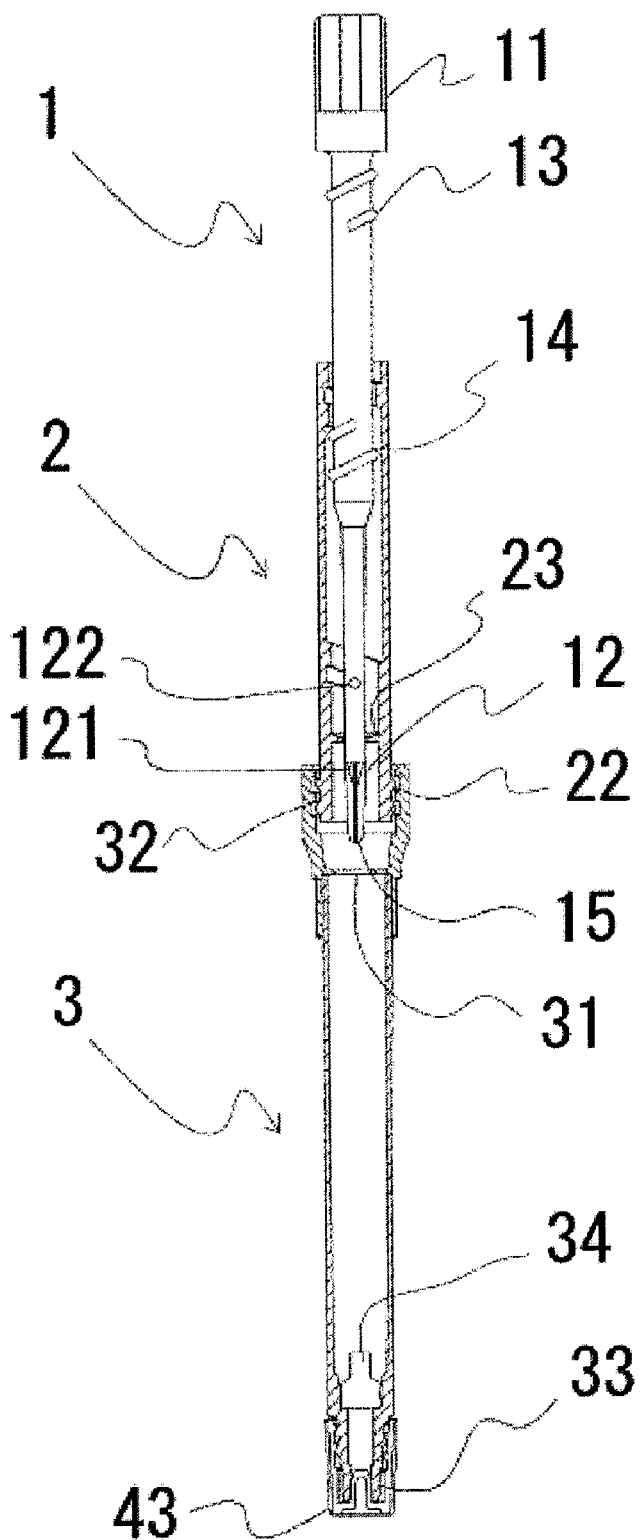
FIG. 5 is a longitudinal cross section of a second example of the feces collection container of the invention.
Figure 6:
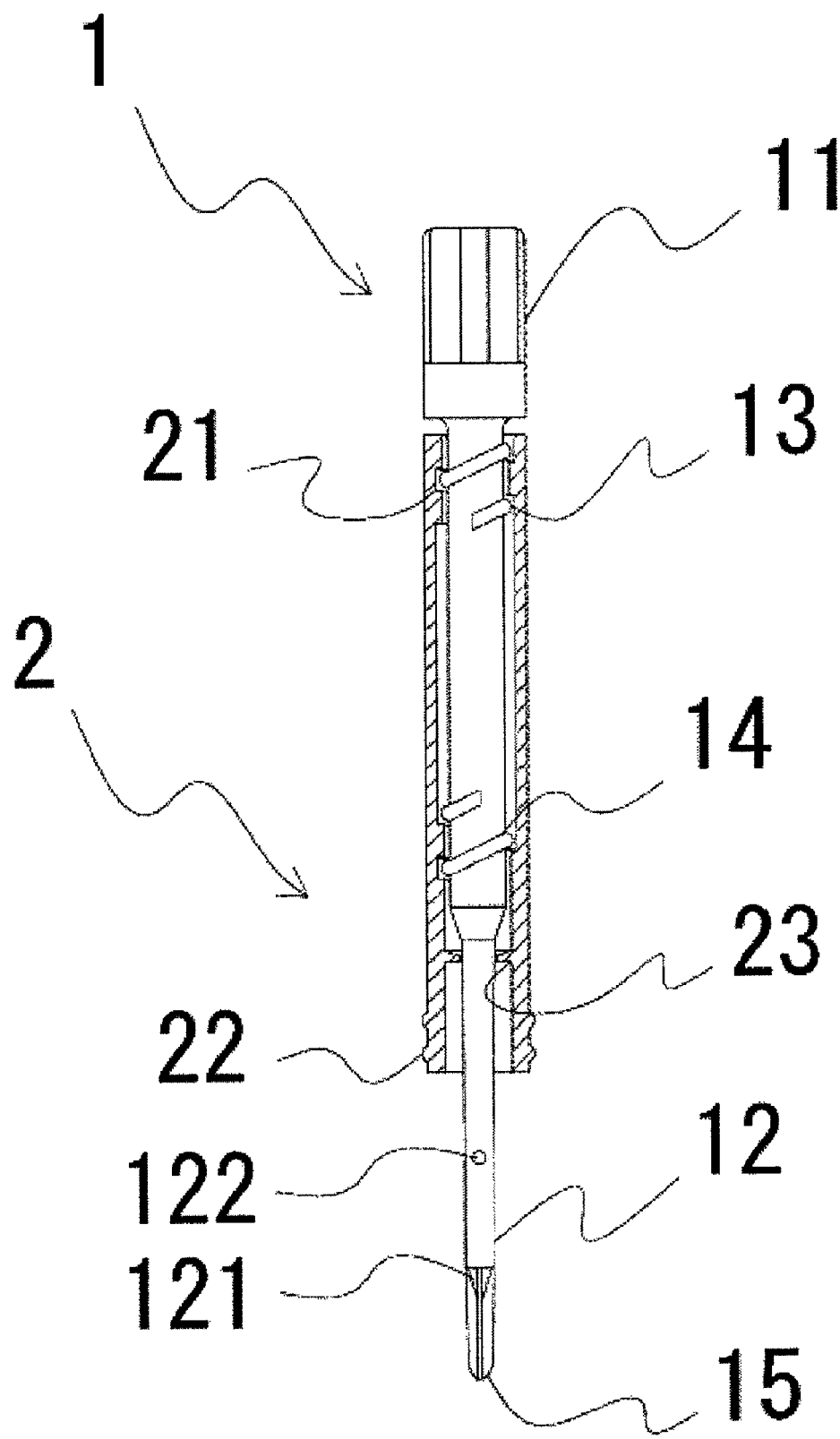
FIG. 6 illustrates the fecal sampling stick and cylindrical member of FIG. 5 while a fecal sample is being obtained.
Figure 7:
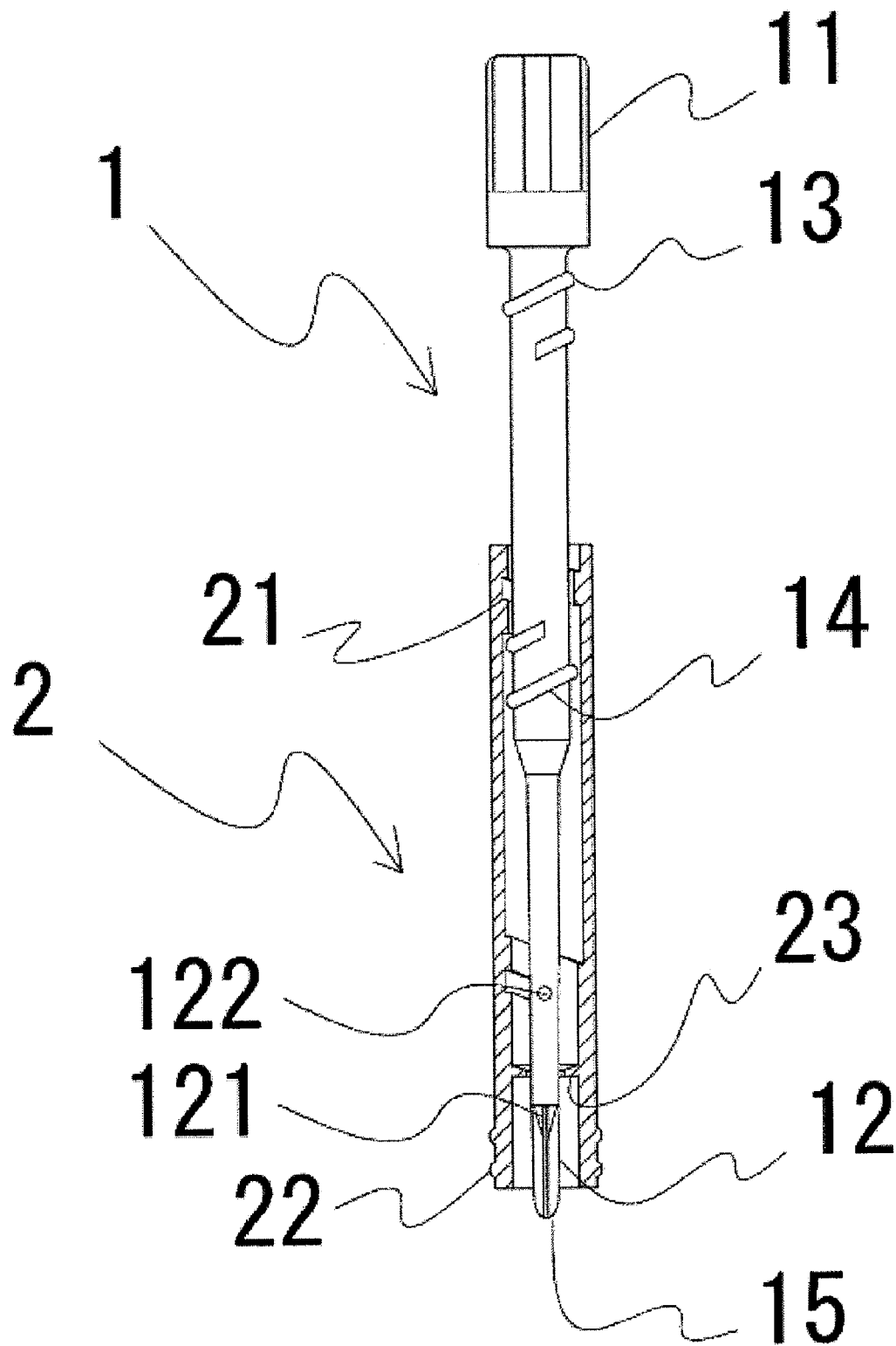
FIG. 7 illustrates the fecal sampling stick of FIG. 6 while retracted.
Figure 8:
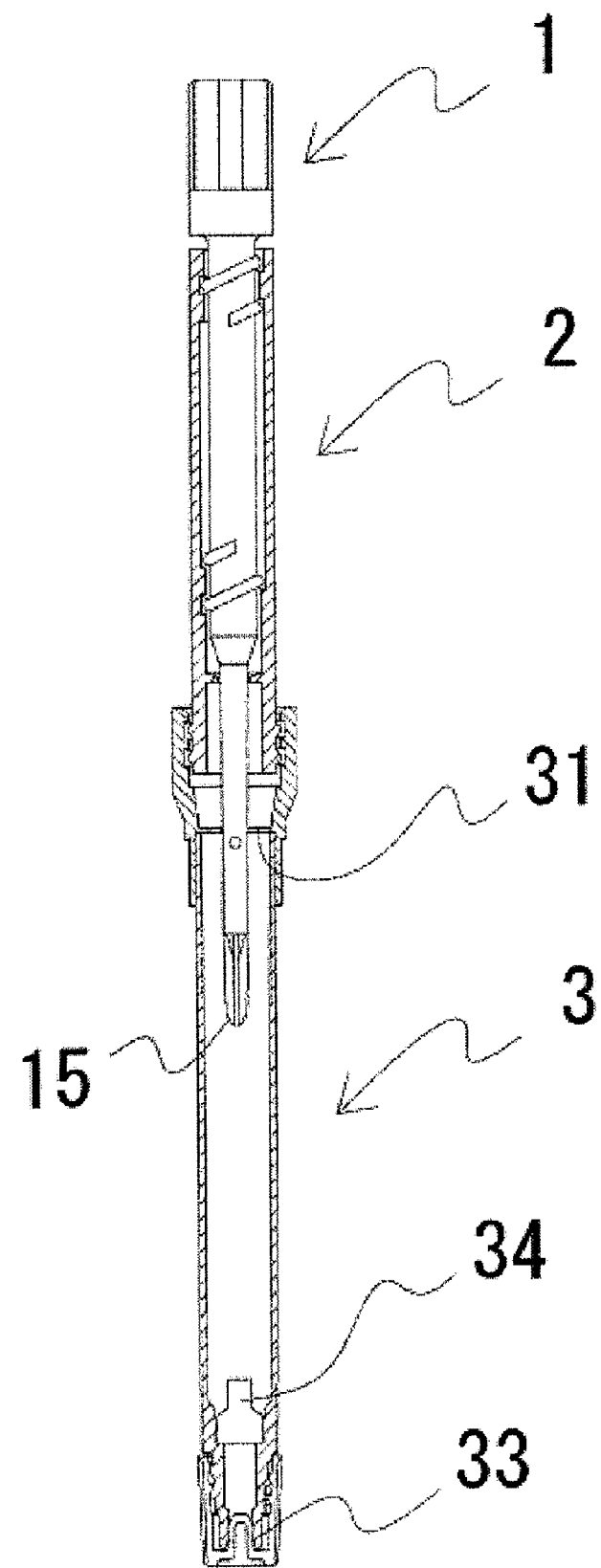
FIG. 8 illustrates the fecal sampling stick of FIG. 5 inserted into the container body.
Figure 9:
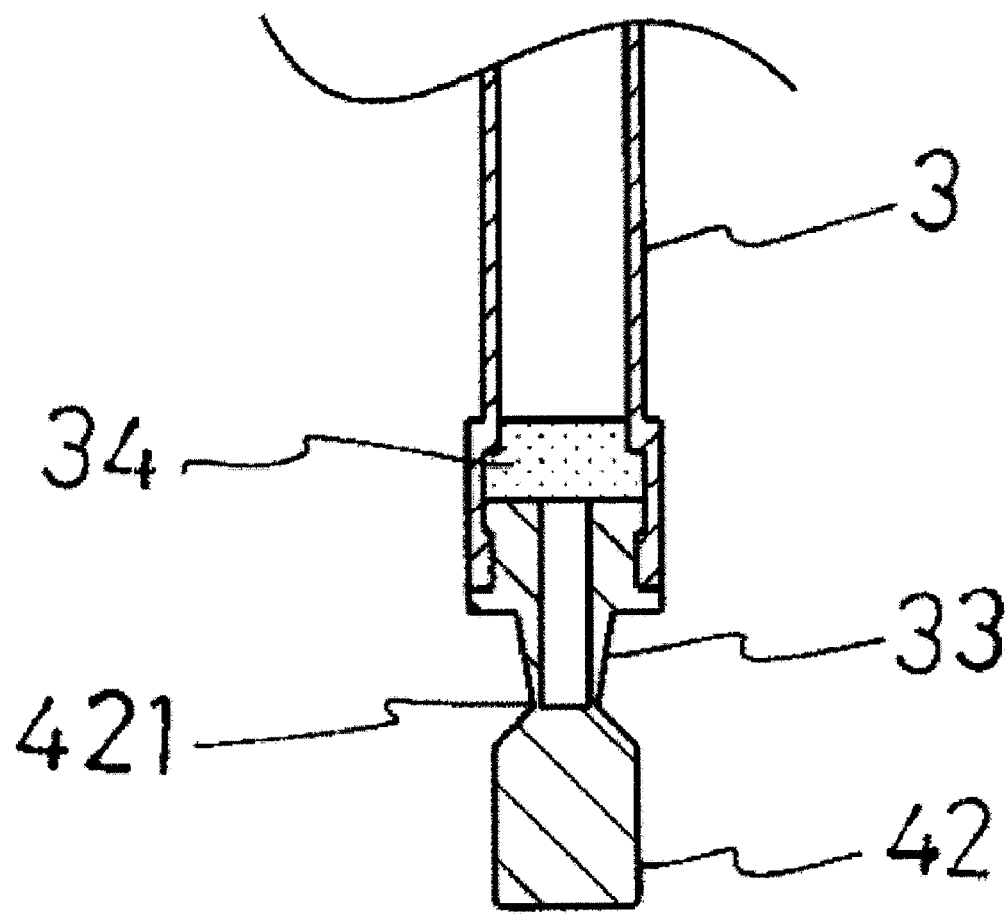
FIG. 9 is a cross section of another example of the drip portion of the feces collection container of the invention.
Figure 10:
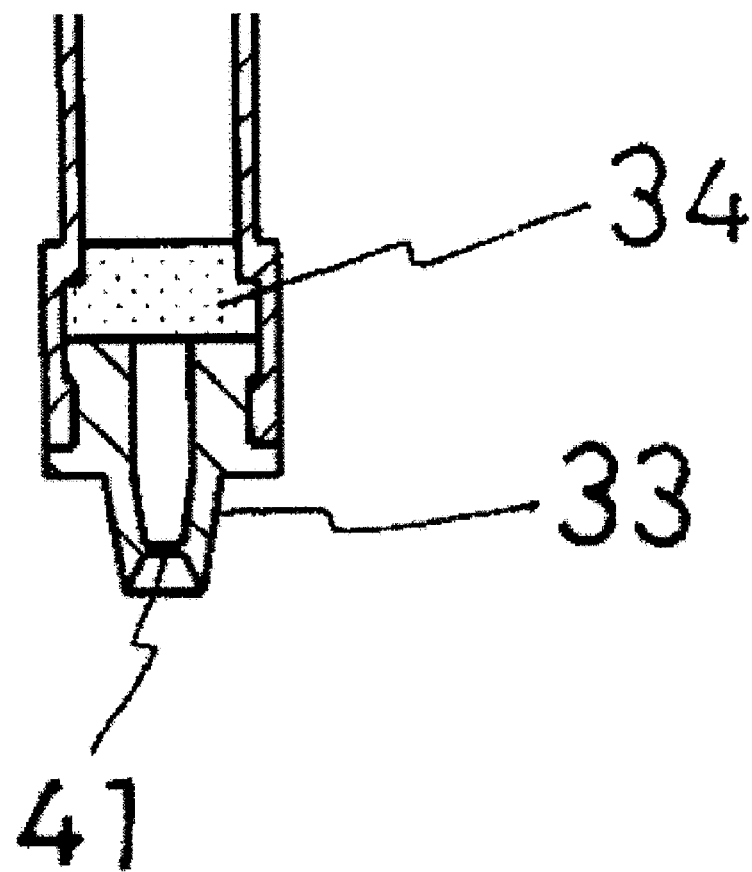
FIG. 10 is a cross section of another example of the drip portion of the feces collection container of the invention.

FIG. 5 is a longitudinal cross section of a second example of the feces collection container of the invention. FIG. 6 illustrates the fecal sampling stick and cylindrical member of FIG. 5 while a fecal sample is being obtained. FIG. 7 illustrates the fecal sampling stick of FIG. 6 while retracted. FIG. 8 illustrates the fecal sampling stick of FIG. 5 inserted into the container body. FIG. 9 is a cross section of another example of the drip portion of the feces collection container of the invention. FIG. 10 is a cross section of another example of the drip portion of the feces collection container of the invention. FIG. 11 is a side view of the protrusion of the fecal sampling stick of the feces collection container of the invention.

Figure 12:
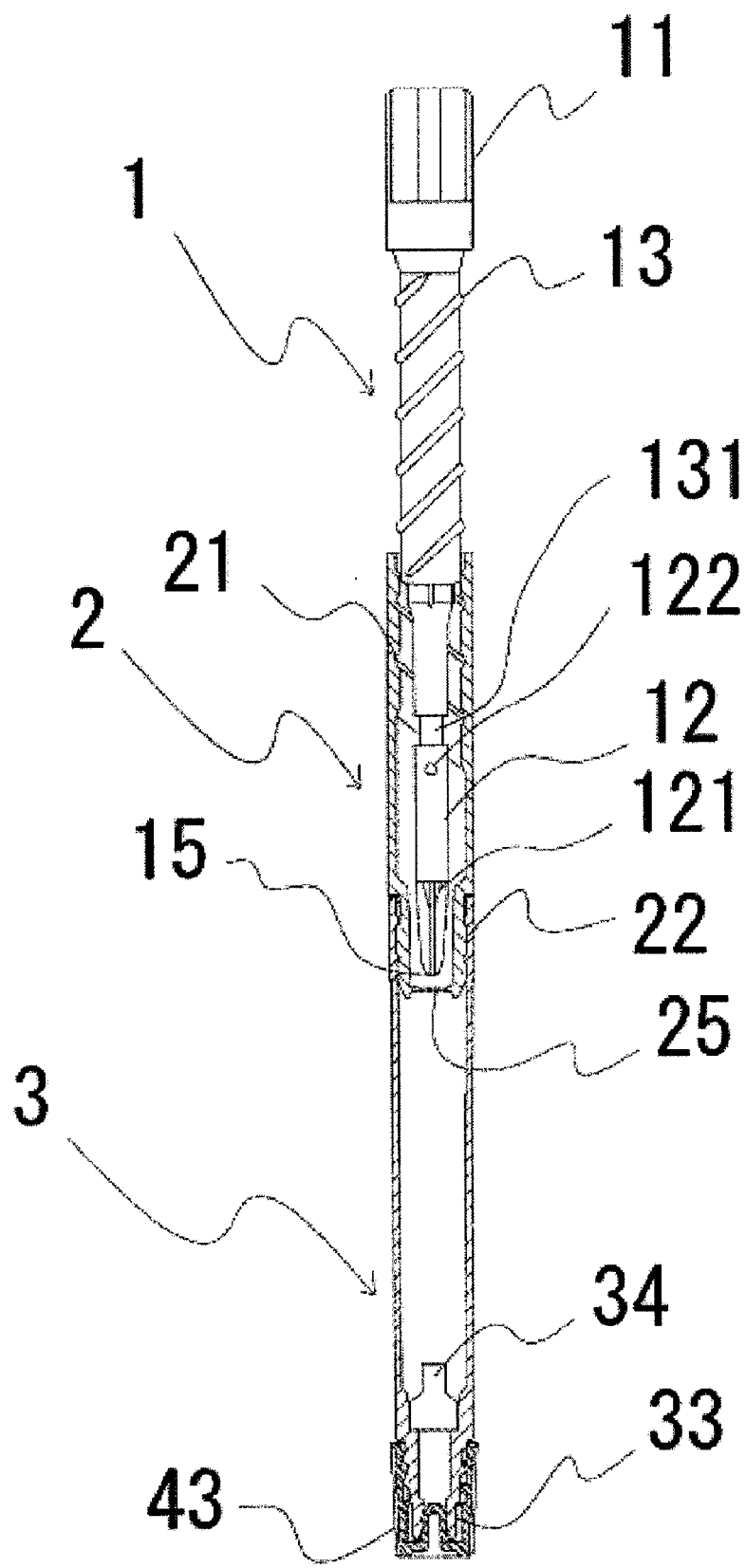
FIG. 12 is a longitudinal cross section of a third example of the feces collection container of the invention.
Figure 13:
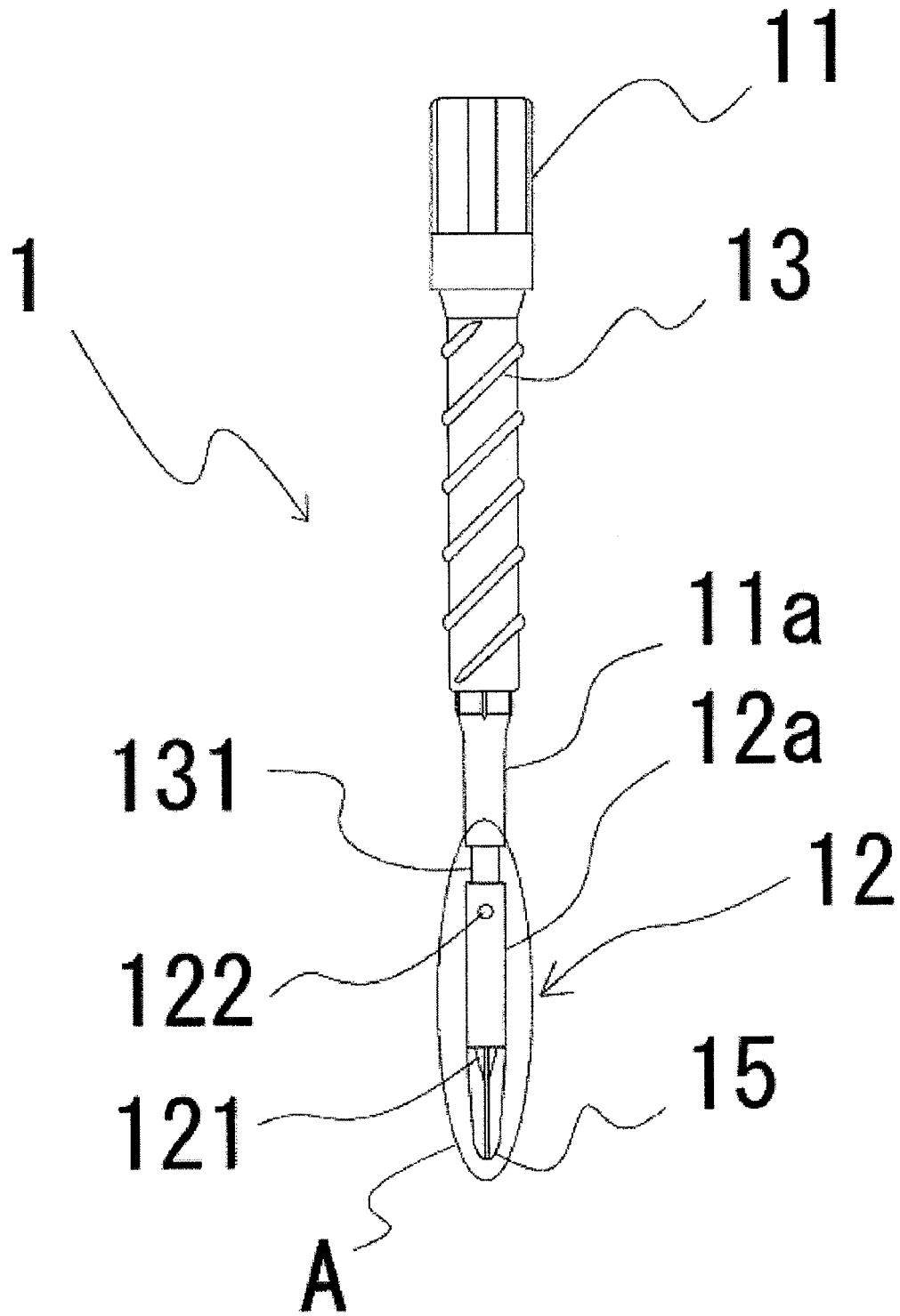
FIG. 13 is a side view of the fecal sampling stick in FIG. 1.
Figure 14:
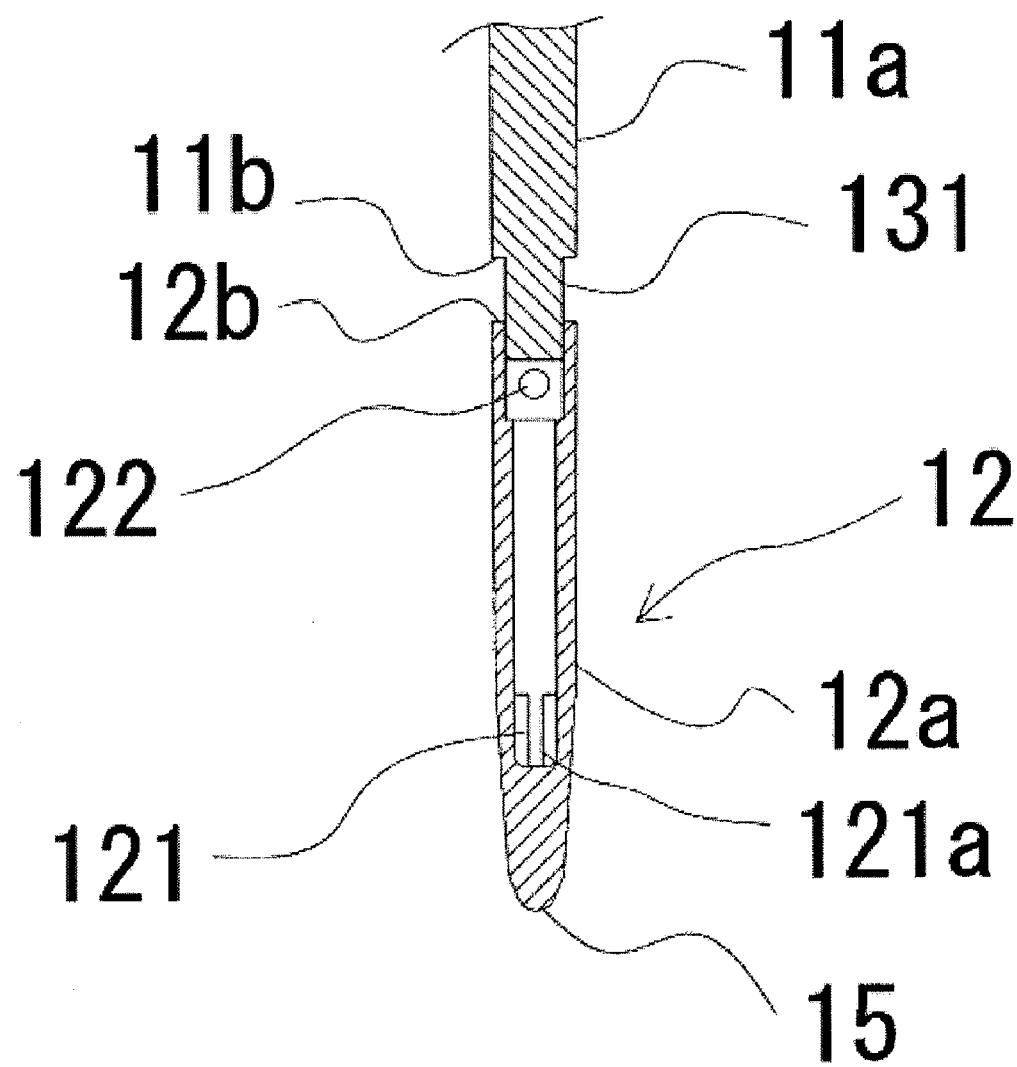
FIG. 14 is a cross sectional detail of portion A in FIG. 13.
Figure 15:
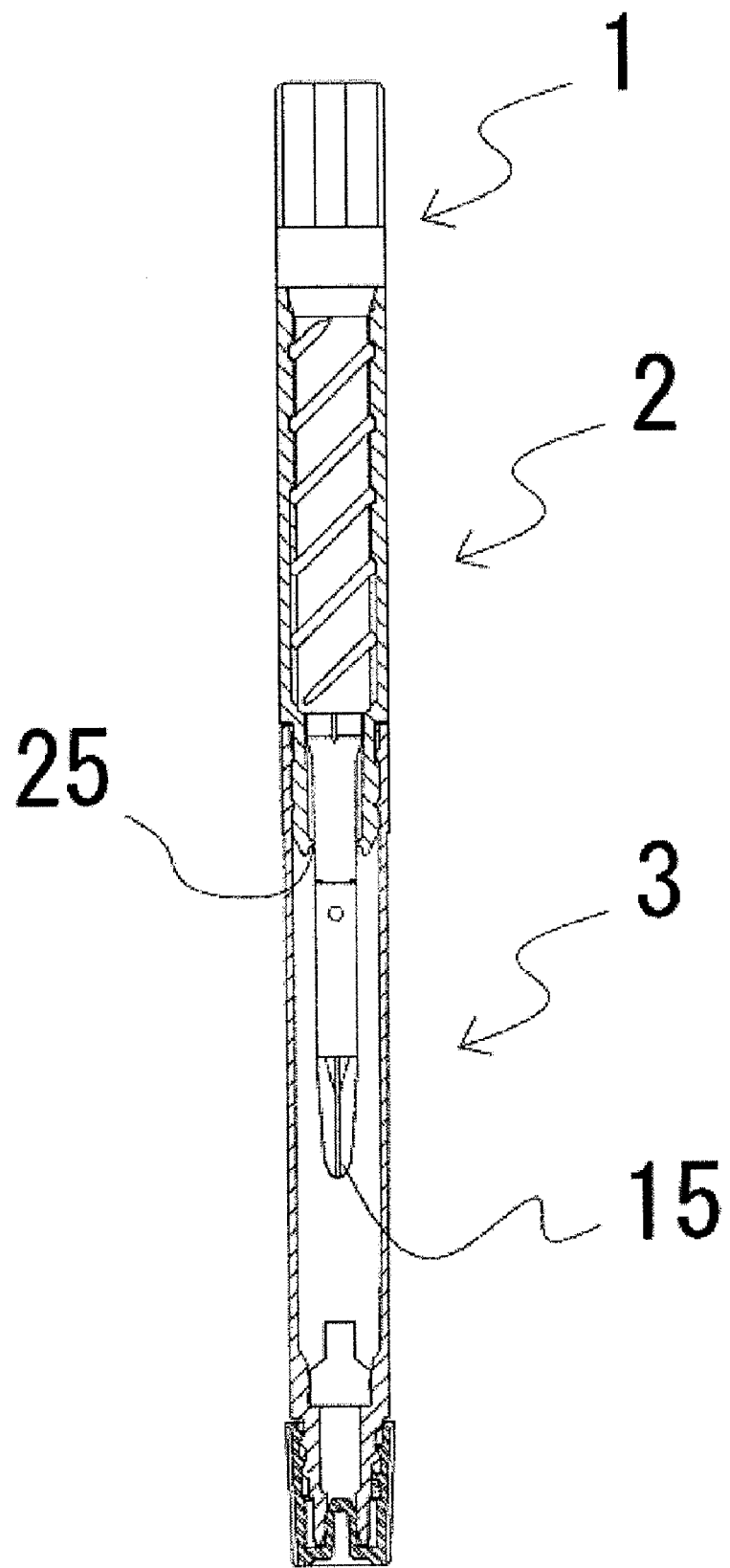
FIG. 15 is a longitudinal cross section of the sealing film penetrated by the fecal sampling stick in the feces collection container illustrated in FIG. 12.
Figure 16:
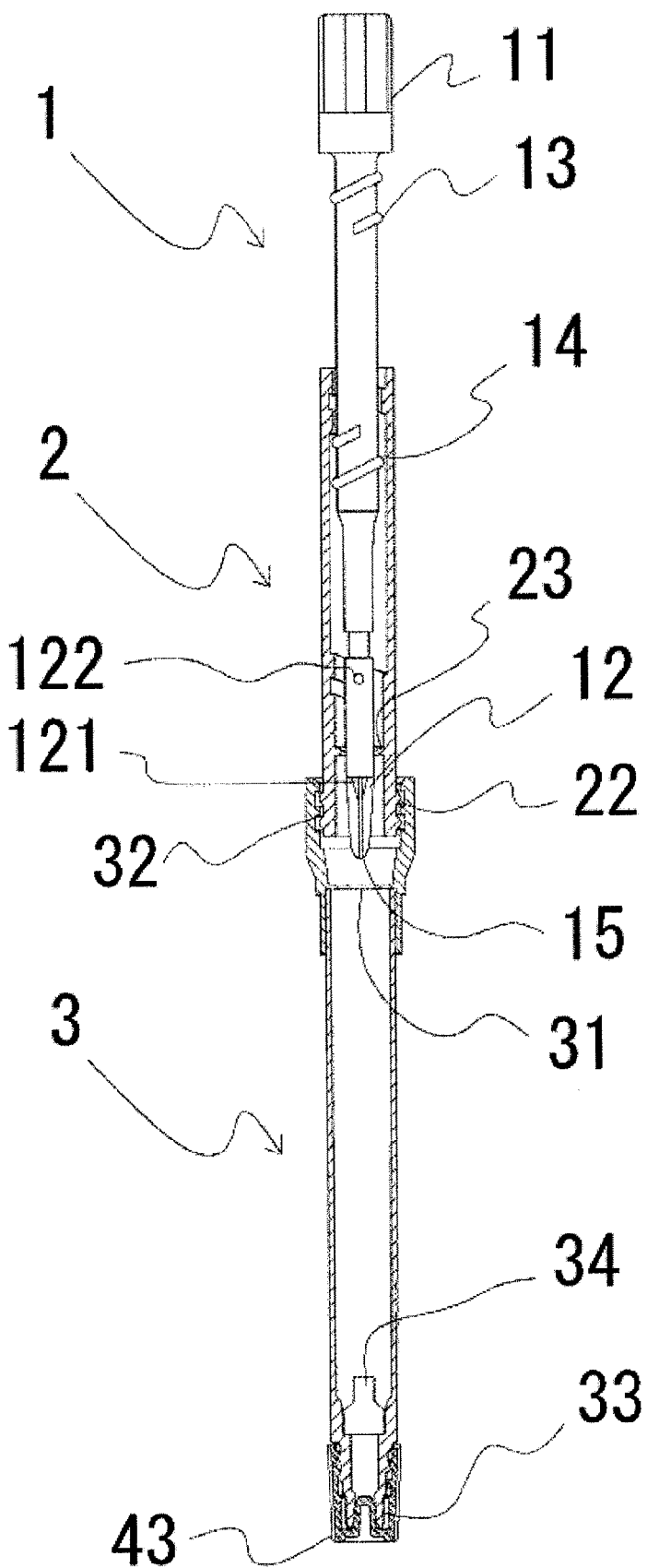
FIG. 16 is a longitudinal cross section of a fourth example of the feces collection container of the invention.
Figure 17:
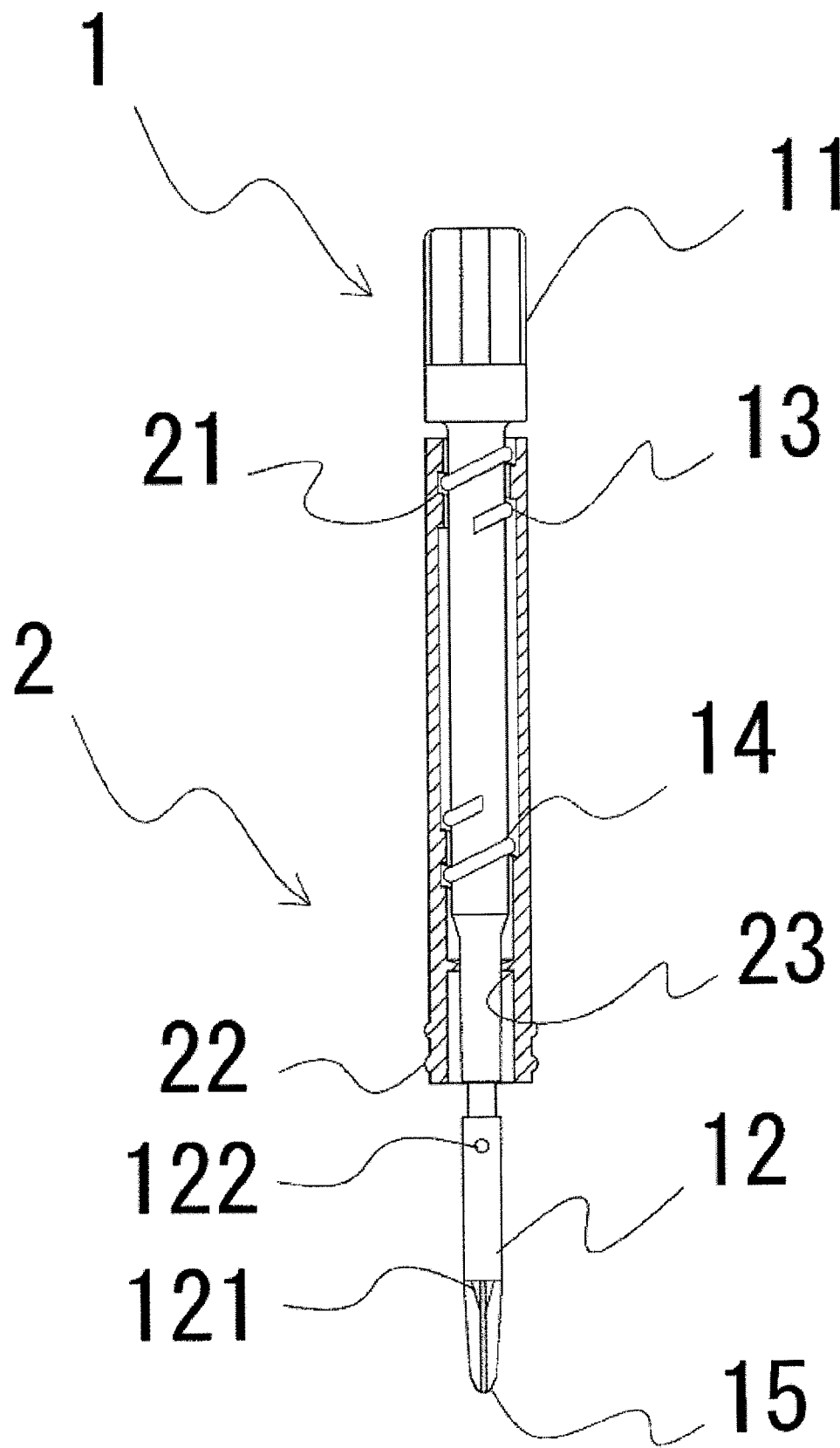
FIG. 17 illustrates the fecal sampling stick and cylindrical member of FIG. 16 while a fecal sample is being obtained.
Figure 18:
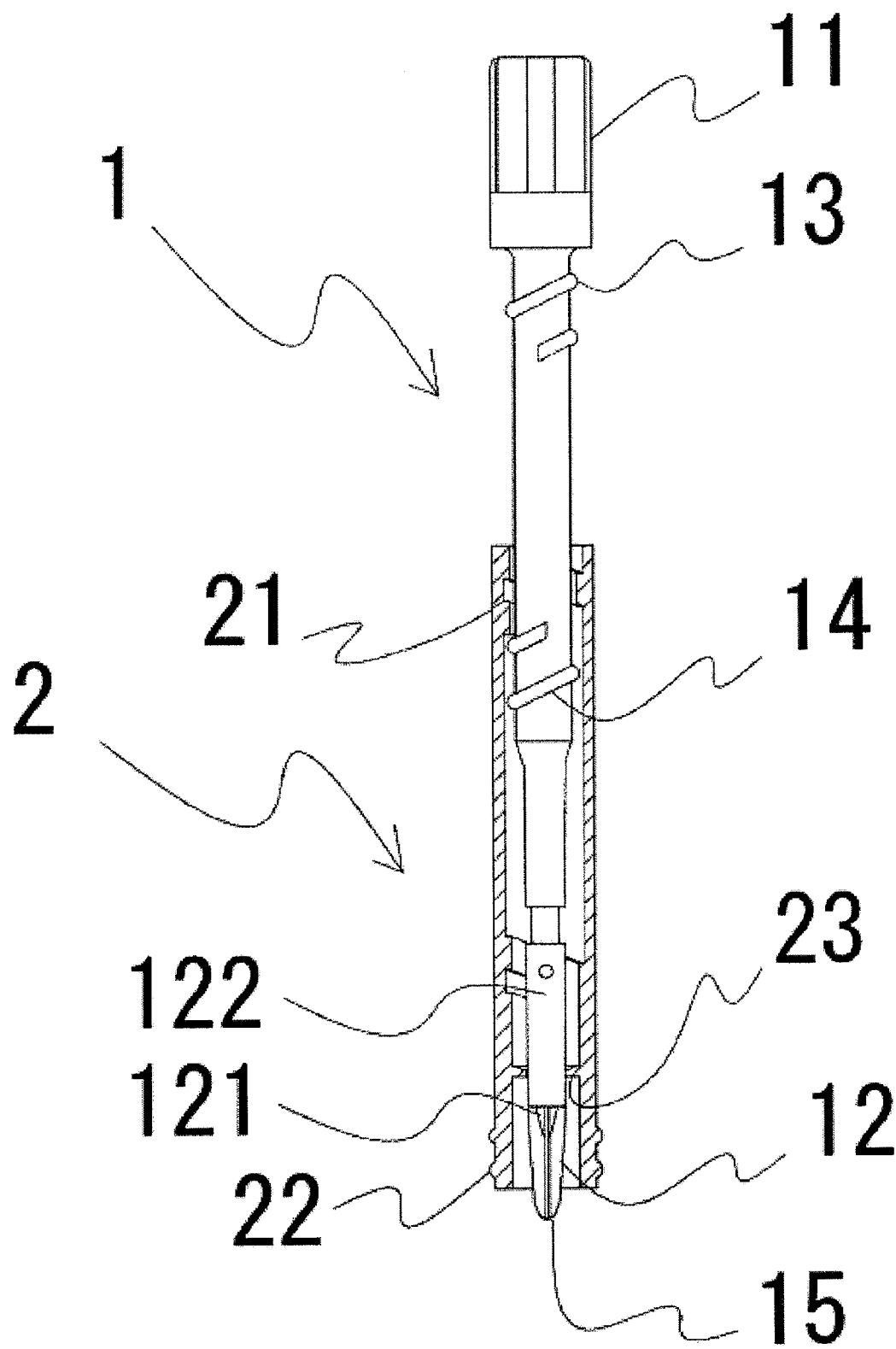
FIG. 18 illustrates the fecal sampling stick of FIG. 17 while retracted.
Figure 19:
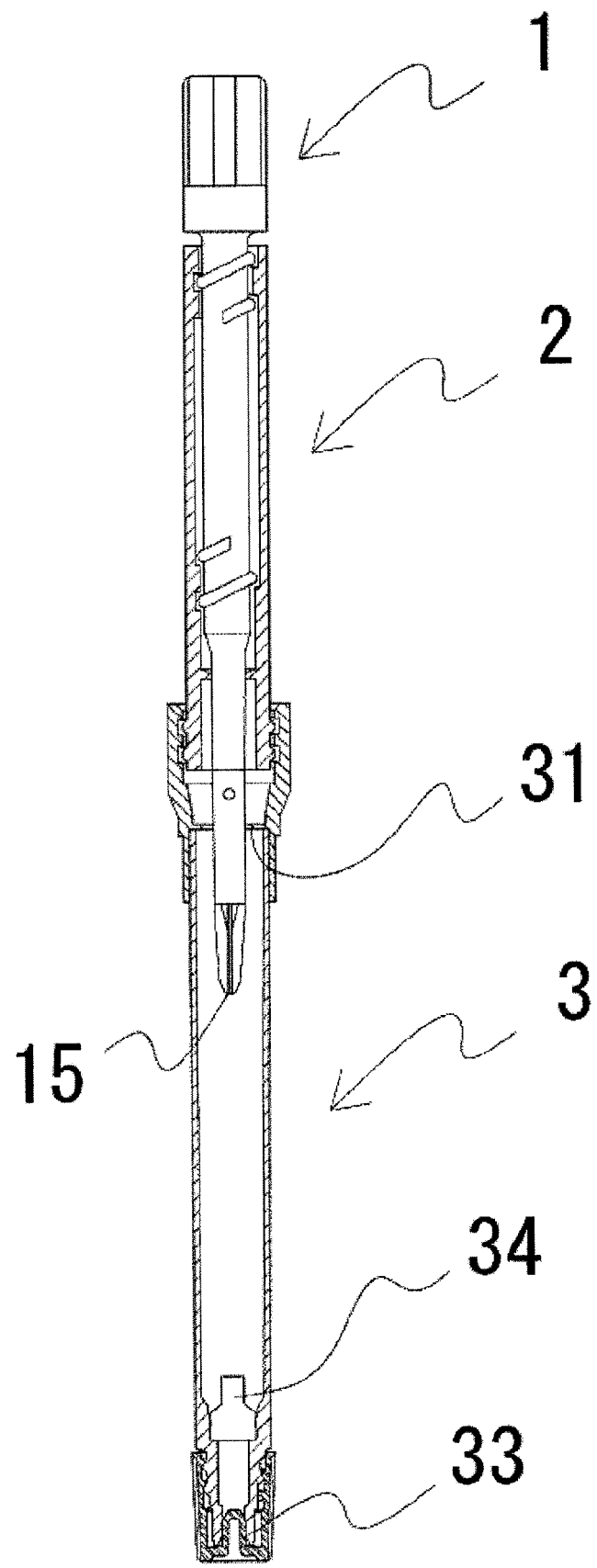
FIG. 19 illustrates the fecal sampling stick of FIG. 16 inserted into the container body.
Figure 20:
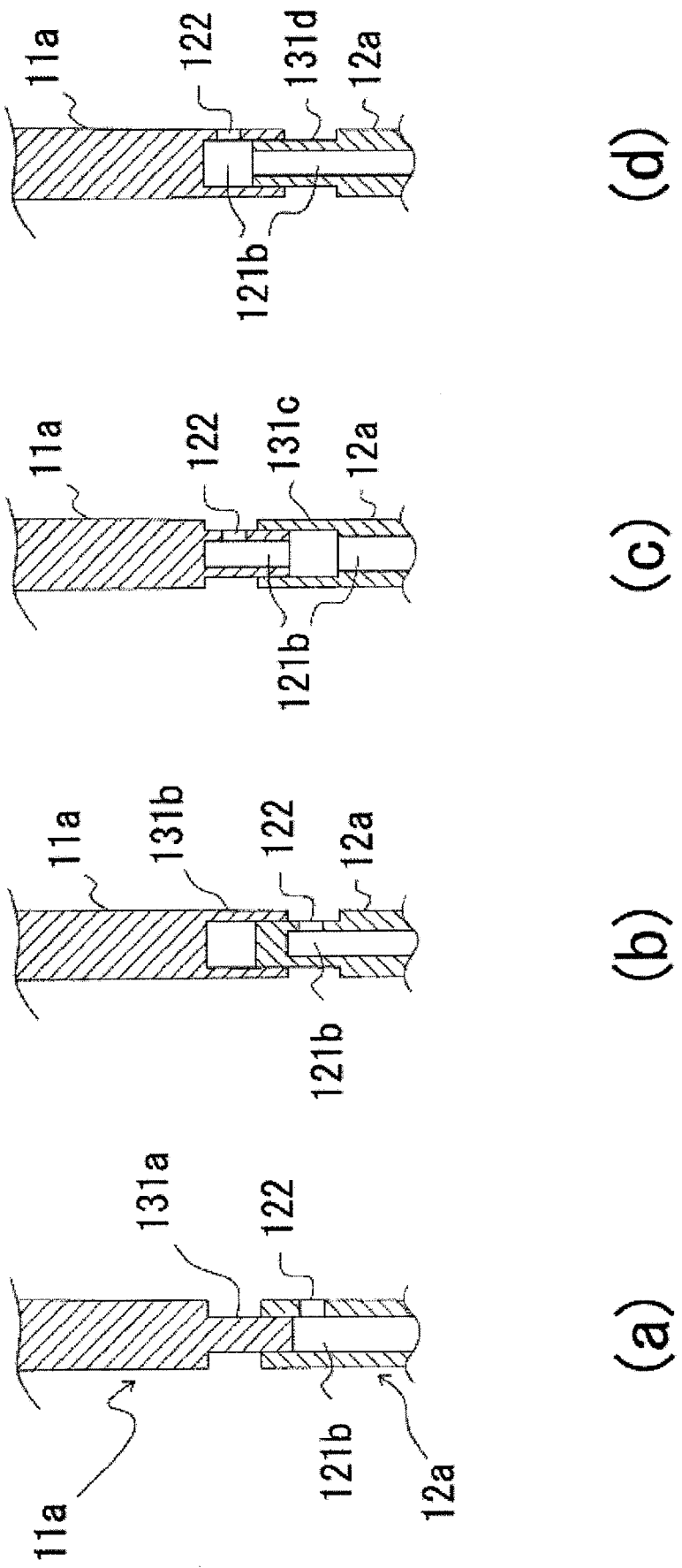
FIG. 20 is a cross section of another example of the opening sealing means in the feces collection container of the invention.

FIG. 12 is a longitudinal cross section of a third example of the feces collection container of the invention. FIG. 13 is a side view of the fecal sampling stick in FIG. 1. FIG. 14 is a cross sectional detail of portion A in FIG. 13. FIG. 15 is a longitudinal cross section of the sealing film penetrated by the fecal sampling stick in the feces collection container illustrated in FIG. 12. FIG. 16 is a longitudinal cross section of a fourth example of the feces collection container of the invention. FIG. 17 illustrates the fecal sampling stick and cylindrical member of FIG. 16 while a fecal sample is being obtained. FIG. 18 illustrates the fecal sampling stick of FIG. 17 while retracted. FIG. 19 illustrates the fecal sampling stick of FIG. 16 inserted into the container body. FIG. 20 is a cross section of another example of the opening sealing means in the feces collection container of the invention.

Example 1

The feces collection container of the invention comprises a fecal sampling stick (1), a cylindrical member (2), and a container body (3), a base of the cylindrical member (2) is open, allowing the fecal sampling stick (1) to be retractably inserted, and a tip is sealed off by a sealing film (25) that can be penetrated by the fecal sampling stick (1); and the tip of the container body (3) is provided with a drip portion (33) that is sealed off by readily openable sealing means (4). An outer wall of the fecal sampling stick (1) and an inner wall of the cylindrical member (2) as well as a tip of the cylindrical member (2) and the base of the container body (3) are engaged in a liquid-tight manner.

According to FIG. 1, the container body (3) is a container in the form of a cylinder that contains a stool-dissolving buffer (not shown) for dissolving the fecal matter sampled by the fecal sampling stick (1). As illustrated in FIG. 1, the base and tip of the container body (3) are equipped with a connecting part of the cylindrical member (2) and a drip portion (33), respectively. The cylindrical member (2) and a drip opening cap (43) are attached to the base and tip, respectively, to partition the fecal dissolving buffer chamber, making it possible to check whether the sample stool has been dissolved. Solutions containing minute amounts of sodium adipate or ammonium chloride as a preservative are generally used as stool-dissolving buffer to dissolve and extract the sampled stool. The container body (3) is gently squeezed on the sides to allow drops of a specimen liquid dissolved and extracted stool sample to be pushed through the drip portion (33). An engagement member (32) is provided at the base to connect in a liquid-tight manner with the tip of the cylindrical member (2), and a rib or an undercut for fitting a concave or convex portion is preferably provided. The connecting part may also be threaded.

The drip portion (33) may be sealed off by readily openable sealing means, and the sealing means may be one that can be removed during use. Desirable examples of such sealing means include a rubber cap (43) shown in FIG. 1, a seal (42)

that can be broken at a fragile part (421) shown in FIG. 9, and the thin film (41) shown in FIG. 10. The cap may be made of a flexible resin such as polyethylene, polypropylene, polyvinyl chloride, polybutadiene, polystyrene, or polyester, as well as butyl rubber or isoprene rubber, etc.

A filter (34) is preferably provided on the base side of the container body (3) adjacent to the drip portion (33), to filter off solids in the stool samples that are obtained. Examples of materials for this part ordinarily include clear flexible resins such as polyethylene, polypropylene, polyvinyl chloride, polybutadiene, polystyrene, or polyester.

The cylindrical member (2) is a member in the form of a cylinder in which the base is open and the tip is sealed off by a sealing film (25), and the barrel diameter is formed preferably about the same as the container body (3). The tip is provided with an engagement member (22) that engages with the engagement member (32) of the container body (3) so as to connect in a liquid-tight manner with the base of the container body (3), and a rib or undercut for fitting a concave or convex portion is preferably provided. The connecting part may also be threaded. On the base side, the connection with the fecal sampling stick (1) is preferably a threaded structure so that the fecal sampling stick (1) can be retractably and detachably attached, and can readily penetrate the sealing film (15) on the tip of the fecal sampling stick (1) after fecal samples have been collected by the fecal sampling stick (1). Specifically, according to FIG. 1, female threading (21) into which male threading (13) of the fecal sampling stick (1) is screwed is provided, protruding out from the inner wall, at the base of the cylindrical member (2), and the male threading (13) and female threading (21) are screwed together when fecal samples are collected and when the fecal sampling portion (12) is housed in the container body (3). Desirable examples of materials for this part ordinarily include clear, soft, flexible resins such as polyethylene, polypropylene, polyvinyl chloride, polybutadiene, or polyester.

As illustrated in FIGS. 2 and 3, the base of the fecal sampling stick (1) has a holding part (11) of relatively large diameter, which is a part that is manually held when collecting fecal samples, and the tip has a fecal sampling part (12) of relatively small diameter to which fecal samples adhere for collection. The portion between the holding part (11) and fecal sampling part (12) has an outside diameter that is somewhat smaller than the inside diameter of the cylindrical member (2), and the outer wall is provided with male threading (13) that screws into the female threading (21) described below that is provided on the inside wall of the cylindrical member (2). The female threading (21) and male threading (13) are screwed together to achieve a liquid-tight seal between the outer wall of the fecal sampling stick (1) and the inner wall of the cylindrical member (2).

The fecal sampling part (12) is elastic and yet hard enough to not break when stool is wiped off and to be able to penetrate the sealing film (25). Examples of materials for the fecal sampling stick (1) usually include flexible resins such as polyethylene, polypropylene, polyester, and ABS.

The fecal sampling part (12) is a hollow structure, the interior of which is a hollow passage with a tip opening and an opening on the base side a certain distance from the tip. The structure is composed of a protrusion (15) at the tip, a hollow aspiration hole (121) in part of the protrusion (15) or adjacently on the base side at a certain distance from the tip opening, and a hole (122) for adjusting the aspiration level, which is open on the base side a certain distance from the tip opening of the aspiration hole (121). The fecal sampling part (12) is preferably transparent or semi-transparent to allow the interior to be visually checked to ensure that watery stool has been sampled. More specifically, the fecal sampling part (12) is preferably a transparent member that is attached, while ensuring liquid-tightness, to the base end of the hole (122) for adjusting the aspiration level. The tip of the protrusion (15) is preferably sharp in order to penetrate the sealing film (25). More specifically, the structure of the protrusion (15) is such that an incision expands so that the fecal sampling part of the fecal sampling stick is inserted into the container body so that excess stool sample can be removed (wiped off) when the fecal sampling part penetrates the sealing film and a fixed quantity of stool sample is collected in the container body. This structure is not limited to simple cones, and may also include, as illustrated in FIG. 11, (a) cross-shaped cross sections, (b) star shapes, and (c) notches. Such notches and holes can be suitably located to allow solid stool to be quantitatively samples.

The holding part (11) usually has ribs provided at certain intervals in the axial direction on the outer peripheral wall of the holding part (11) so that it is easier to grasp in order to facilitate attachment and detachment by a threaded structure between it and the cylindrical member (2).

The shape and size of the aspiration hole (121) is such as to break the surface tension in order to allow liquid stool such as diarrhea or watery stool to be effectively samples. The shape is preferably oblong or rectangular. There may also be one or more aspiration holes (121). These can be freely selected, in anticipation differences in stool or the like depending on ethnicity. Hydrophilization by corona discharge, plasma treatment, or the like is also preferred, particularly as aspiration will be easier under conditions where the contact angle is smaller and the surface tension is greater, such as when the surface tension is generally represented by the following Formula (A).

$$\text{liquid level ascending height }(m)h=2T\cos\theta/\rho gr \quad \text{Formula (A)}$$

T: surface tension (N/m); θ: contact angle (deg); ρ: fluid density (kg/m$^3$);

g: acceleration of gravity (m/sec$^2$); r: radius of tube (m)

Furthermore, to prevent aspirated stool from immediately leaking out of the aspiration hole (121) because of gravity, the aspiration hole (121) is preferably located on the side or is shrunk depthward.

The position where the hole (122) for adjusting the aspiration level is located a certain distance behind the aspiration hole (121) can be freely selected to ensure that enough liquid stool such as diarrhea or watery stool is aspirated for analysis on the basis of a volume of the hollow structure of the fecal sampling part. There may be one or more holes (122) for adjusting the aspiration level, provided that the strength of the fecal sampling part (12) is not compromised. The fecal sampling stick (1) is preferably secured with a seal or the like (not shown) that covers the stick in such a way as to span the outer peripheral wall of the base of the cylindrical member (2) and the outer peripheral wall of the holding part (11) of the fecal sampling stick (1), so that the fecal sampling part is held in a position where it will not perforate the sealing film (25).

The use of the feces collection container of the invention will be described below with reference to drawings.

When preparing the suspension, the seal or the like (not shown) securing the fecal sampling stick (1) is first taken out of the feces collection container, and the holding part (11) of the fecal sampling stick (1) is rotated so that the male threading (13) of the fecal sampling stick (1) is detached from the female threading (21) of the cylindrical member (2). The fecal sampling part (12) is then brought down into contact with the surface of the stool that is to be analyzed and scrape to collect the sample.

When the stool is a liquid such as diarrhea or watery stool, the fecal sampling part (12) is brought down and stirred in the liquid while the aspiration hole (121) is submerged below the surface of the stool liquid to collect the sample.

The opening at the base of the cylindrical member (2) is then oriented upward, the fecal sampling part (12) of the fecal sampling stick (1) is then carefully inserted deeply, the male threading (14) of the fecal sampling stick (1) and the female threading (21) of the cylindrical member (2) are screwed together to advance the fecal sampling stick (1) forward, and the sealing film (25) of the cylindrical member (2) is penetrated by the fecal sampling stick (1) to wipe of the excess stool sample adhering to the fecal sampling part (12), allowing a certain amount of the fecal sample to be collected in the container body (3).

The male threading (13) of the fecal sampling stick (1) and the female threading (21) of the cylindrical member (2) are screwed together (see FIG. 4) to ensure a liquid-tight seal between the outer wall of the fecal sampling stick (1) and the inner wall of the cylindrical member (2) to prevent leakage of the fecal sample that has been naturally dissolved and suspended in the stool-dissolving buffer in the interior (referred to below as analyte). In addition, at this time, the hole (122) for adjusting the aspiration level can also be positioned in advance to be more toward the distal end side from the sealing film (25) when the male threading (13) of the fecal sampling stick (1) and the female threading (21) of the cylindrical member (2) are screwed together, preventing the fecal sample from leaking. The cap (43) can be taken off the drip portion (33) to allow drops of analyte to be poured out the drip portion (33) for analysis.

Example 2

Another feces collection container of the invention will be described below with reference to drawings.

As illustrated in FIG. 5, the feces collection container of the invention comprises a fecal sampling stick (1), a cylindrical member (2), and a container body (3), wherein the cylindrical member (2) is open at both ends so that the fecal sampling stick (1) is retractably inserted, the base of the container body (3) is sealed with a sealing film (31) that can be penetrated by the fecal sampling stick (1), and the tip is provided with a drip portion (33) that is sealed off by readily openable sealing means (4). The outer wall of the fecal sampling stick (1) and the inner wall of the cylindrical member (2) as well as the tip of the cylindrical member (2) and the base of the container body (3) are engaged in a liquid-tight manner, respectively.

The differences from the feces collection container illustrated in FIG. 1 are that the sealing membrane is provided in the container moan body (3), not the cylindrical member (2), and the cylindrical member (2) is integrally attachable and detachable with the fecal sampling stick (1), allowing the fecal sampling part (12) to be retractably operated.

When preparing the suspension, the cylindrical member (2) is first taken out of the container body (3). The seal or the like (not shown) securing the fecal sampling stick (1) is then taken out of the feces collection container, and the holding part (11) of the fecal sampling stick (1) is rotated to advance and expose the fecal sampling part (12). The fecal sampling part (12) is then brought down into contact with the surface of the stool that is to be analyzed and scrape to collect the sample. When the stool is a liquid such as diarrhea or watery stool, the fecal sampling part (12) is brought down and stirred in the liquid while the aspiration hole (121) is submerged below the surface of the stool liquid to collect the sample. The male threading (13) of the fecal sampling stick (1) is detached from the female threading (21) of the cylindrical member (2) to back off the fecal sampling stick (1), and the male threading (14) and female threading (21) are screwed together, allowing the fecal sampling part (12) to be housed in the cylindrical member (2) as illustrated in FIG. 7. A ring-shaped protrusion (23) is provided on the inner wall on the base side from the position where the fecal sampling part (12) of the cylindrical member (2) is retracted, so that there is no risk of excess stool flowing to the base side of the cylindrical member (2).

Then, the engagement part (22) of the cylindrical member (2) is engaged with the engagement part (32) of the container body (3) (resulting in liquid-tightness between the outer wall of the cylindrical member (2) and the inner wall of the container body (3)), the male threading (14) of the fecal sampling stick (1) and the female threading (21) of the cylindrical member (2) are then unscrewed to advance the fecal sampling stick (1) forward, and the sealing film (31) of the container body (3) is penetrated by the fecal sampling stick (1) to wipe of the excess stool sample adhering to the fecal sampling part (12), allowing a certain amount of the fecal sample to be collected in the container body (3).

The male threading (13) of the fecal sampling stick (1) and the female threading (21) of the cylindrical member (2) are screwed together (see FIG. 8) to ensure a liquid-tight seal between the outer wall of the fecal sampling stick (1) and the inner wall of the cylindrical member (2) to prevent leakage of the fecal sample that has been naturally dissolved and suspended in the stool-dissolving buffer in the interior (referred to below as analyte). In addition, at this time, the hole (122) for adjusting the aspiration level can also be positioned in advance to be more toward the distal end side from the sealing film (25) when the male threading (13) of the fecal sampling stick (1) and the female threading (21) of the cylindrical member (2) are screwed together, preventing the fecal sample from leaking. The thin film 41 of the drip portion (33) can be penetrated with a special spike (not shown) or the like to allow drops of analyte to be poured out the drip portion (33) for analysis.

Example 3

The feces collection container of the invention comprises a fecal sampling stick (1), a cylindrical member (2), and a container body (3), a base of the cylindrical member (2) is open, allowing the fecal sampling stick (1) to be retractably inserted, and a tip is sealed off by a sealing film (25) that can be penetrated by the fecal sampling stick (1); and the tip of the container body (3) is provided with a drip portion (33) that is sealed off by readily openable sealing means (4). An outer wall of the fecal sampling stick (1) and an inner wall of the cylindrical member (2) as well as a tip of the cylindrical member (2) and the base of the container body (3) are engaged in a liquid-tight manner.

According to FIG. 12, the container body (3) is a container in the form of a cylinder that contains a stool-dissolving buffer (not shown) for dissolving the fecal matter sampled by the fecal sampling stick (1). As illustrated in FIG. 12, the base and tip of the container body (3) are equipped with a connecting part of the cylindrical member (2) and a drip portion (33), respectively. The cylindrical member (2) and a drip opening cap (43) are attached to the base and tip, respectively, to partition the fecal dissolving buffer chamber, making it possible to check whether the sample stool has been dissolved. Solutions containing minute amounts of sodium adipate or ammonium chloride as a preservative are generally used as stool-dissolving buffer to dissolve and extract the sampled stool. The container body (3) is gently squeezed on the sides to allow drops of a specimen liquid dissolved and extracted stool sample to be pushed through the drip portion (33). An engagement member (32) is provided at the base to connect in a liquid-tight manner with the tip of the cylindrical member (2), and a rib or an undercut for fitting a concave or convex portion is preferably provided. The connecting part may also be threaded.

The drip portion (33) may be sealed off by readily openable sealing means, and the sealing means may be one that can be removed during use. Desirable examples of such sealing means include a rubber cap (43) shown in FIG. 12, a seal (42) that can be broken at a fragile part (421) shown in FIG. 9, and the thin film (41) shown in FIG. 10. The cap may be made of a flexible resin such as polyethylene, polypropylene, polyvinyl chloride, polybutadiene, polystyrene, or polyester, as well as butyl rubber or isoprene rubber, etc.

A filter (34) is preferably provided on the base side of the container body (3) adjacent to the drip portion (33), to filter off solids in the stool samples that are obtained. Examples of materials for this part ordinarily include clear flexible resins such as polyethylene, polypropylene, polyvinyl chloride, polybutadiene, polystyrene, or polyester.

The cylindrical member (2) is a member in the form of a cylinder in which the base is open and the tip is sealed off by a sealing film (25), and the barrel diameter is formed preferably about the same as the container body (3). The tip is provided with an engagement member (22) that engages with the engagement member (32) of the container body (3) so as to connect in a liquid-tight manner with the base of the container body (3), and a rib or undercut for fitting a concave or convex portion is preferably provided. The connecting part may also be threaded. On the base side, the connection with the fecal sampling stick (1) is preferably a threaded structure so that the fecal sampling stick (1) can be retractably and detachably attached, and can readily penetrate the sealing film (15) on the tip of the fecal sampling stick (1) after fecal samples have been collected by the fecal sampling stick (1). Specifically, according to FIG. 12, female threading (21) into which male threading (13) of the fecal sampling stick (1) is screwed is provided, protruding out from the inner wall, at the base of the cylindrical member (2), and the male threading (13) and female threading (21) are screwed together when fecal samples are collected and when the fecal sampling portion (12) is housed in the container body (3). Desirable examples of materials for this part ordinarily include clear, soft, flexible resins such as polyethylene, polypropylene, polyvinyl chloride, polybutadiene, or polyester.

As illustrated in FIGS. 13 and 14, the base of the fecal sampling stick (1) has a holding part (11) of relatively large diameter, which is a part that is manually held when collecting fecal samples, and the tip has a fecal sampling part (12) of relatively small diameter to which fecal samples adhere for collection. The portion between the holding part (11) and fecal sampling part (12) has an outside diameter that is somewhat smaller than the inside diameter of the cylindrical member (2), and the outer wall is provided with male threading (13) that screws into the female threading (21) described below that is provided on the inside wall of the cylindrical member (2). The female threading (21) and male threading (13) are screwed together to achieve a liquid-tight seal between the outer wall of the fecal sampling stick (1) and the inner wall of the cylindrical member (2).

The fecal sampling part (12) is elastic and yet hard enough to not break when stool is wiped off and to be able to penetrate the sealing film (25). Examples of materials for the fecal sampling stick (1) usually include flexible resins such as polyethylene, polypropylene, polyester, and ABS.

The fecal sampling part (12) is a hollow structure, the interior of which is a hollow passage with a tip opening and a base side opening on the base side a certain distance from the tip. The structure is composed of a protrusion (15) at the tip, a aspiration hole (121) which is a hollow (121b) extended from a tip opening (121a) in part of the protrusion (15) or adjacently, and a hole (122) for adjusting the aspiration level, which is the base side opening and is open on the base side a certain distance from the tip opening of the aspiration hole (121). The feces collection container of the invention is provides with an opening closing means which can be seal with a liquid-tight the hole (122) for adjusting the aspiration level.

The fecal sampling stick (1) is composed of a fecal sampling part side member (12a) and a holding part side member (11a), where the base of the fecal sampling part side member (12a) and the tip of the holding part side member (11a) are relatively displaceably slidingly connected. The hole (122) for adjusting the aspiration level is in the base of the fecal sampling part side member (12a), and the tip of the holding part side member (11a) has a protrusion (131), which is an opening closing means relatively displaced from the position where the hole (122) for adjusting the aspiration level is open to the position where it is closed.

Specifically, in FIGS. 13 and 14, the tip of the holding part (11) is usually provided with the protrusion (131) that is slidably attached in a liquid-tight manner to the inner wall of the base of the fecal sampling part (12). Prior to operation, the protrusion (131) serving as the opening closing means of the tip of the holding part (11) is disposed at a position where the hole (122) for adjusting the aspiration level is open, the fecal sampling part (12) slides to the base side with perforation resistance at the time the fecal sampling stick (1) penetrates the sealing film (25) to insert the fecal sampling part (12) of the fecal sampling stick (1) inside the container body, and the hole (122) for adjusting the aspiration level is closed.

That is, the perforation resistance during the penetration of the sealing film (25) by the fecal sampling stick (1) allows the base of the of the fecal sampling part side member (12a) and the tip of the holding part side member (11a) to slide, and the protrusion (131) serving as the opening closing means is relatively displaced from the position where the hole (122) for adjusting the aspiration level is open to the position where it is closed. Specifically, when a sample is collected by the fecal sampling stick (1), the fecal sampling part side member (12a) and the holding part side member (11a) are held by detent means, not shown, at the position (position shown in FIGS. 13 and 14) where the protrusion (131) opens the hole (122) for adjusting the aspiration level, as illustrated. As the holding force is set to be lower than the penetration resistance during the penetration of the sealing film (25) by the fecal sampling stick (1), the protrusion (131) slides from the position where the hole (122) for adjusting the aspiration level is open to the position where it is closed during the penetration of the sealing film (25) by the fecal sampling stick (1). The end (12b) of the fecal sampling part side member (12a) and the end (11b) of the holding part side member (11a) then come into contact, and the protrusion (131) is held in the position where the hole (122) for aspiration level is closed.

The fecal sampling part (12) is preferably transparent or semi-transparent to allow the interior to be visually checked to ensure that watery stool has been sampled. The tip of the protrusion (15) is preferably sharp in order to penetrate the sealing film (25). More specifically, the structure of the protrusion (15) is such that an incision expands so that the fecal sampling part of the fecal sampling stick is inserted into the container body so that excess stool sample can be removed (wiped off) when the fecal sampling part penetrates the sealing film and a fixed quantity of stool sample is collected in the container body. This structure is not limited to simple cones, and may also include, as illustrated in FIG. 11, (a) cross-shaped cross sections, (b) star shapes, and (c) notches. Such notches and holes can be suitably located to allow solid stool to be quantitatively samples.

The holding part (11) usually has ribs provided at certain intervals in the axial direction on the outer peripheral wall of the holding part (11) so that it is easier to grasp in order to facilitate attachment and detachment by a threaded structure between it and the cylindrical member (2).

The shape and size of the aspiration hole (121) is such as to break the surface tension in order to allow liquid stool such as diarrhea or watery stool to be effectively samples. The shape is preferably oblong or rectangular. There may also be one or more aspiration holes (121). These can be freely selected, in anticipation differences in stool or the like depending on ethnicity. Hydrophilization by corona discharge, plasma treatment, or the like, or formation of fine projections is also preferred, particularly as aspiration will be easier under conditions where the contact angle is smaller and the surface tension is greater, such as when the surface tension is generally represented by the following Formula (A).

liquid level ascending height $(m)h=2T\cos\theta/\rho gr$   Formula (A)

T: surface tension (N/m); θ: contact angle (deg); ρ: fluid density (kg/m$^3$);

g: acceleration of gravity (m/sec$^2$); r: radius of tube (m)

Furthermore, to prevent aspirated stool from immediately leaking out of the aspiration hole (121) because of gravity, the aspiration hole (121) is preferably located on the side or is shrunk depthward.

The position where the hole (122) for adjusting the aspiration level is located at the base a certain distance behind the aspiration hole (121) can be freely selected to ensure that enough liquid stool such as diarrhea or watery stool is aspirated for analysis on the basis of a volume of the hollow structure of the fecal sampling part. There may be one or more holes (122) for adjusting the aspiration level, provided that the strength and the degree of closure of the fecal sampling part (12) is not compromised.

The fecal sampling stick (1) is preferably secured with a seal or the like (not shown) that covers the stick in such a way as to span the outer peripheral wall of the base of the cylindrical member (2) and the outer peripheral wall of the holding part (11) of the fecal sampling stick (1), so that the fecal sampling part is held in a position where it will not perforate the sealing film (25).

The use of the feces collection container of the invention will be described below with reference to drawings.

When preparing the suspension, the seal or the like (not shown) securing the fecal sampling stick (1) is first taken out of the feces collection container, and the holding part (11) of the fecal sampling stick (1) is rotated so that the male threading (13) of the fecal sampling stick (1) is detached from the female threading (21) of the cylindrical member (2). The fecal sampling part (12) is then brought down into contact with the surface of the stool that is to be analyzed and scrape to collect the sample.

When the stool is a liquid such as diarrhea or watery stool, the fecal sampling part (12) is brought down and stirred in the liquid while the aspiration hole (121) is submerged below the surface of the stool liquid to collect the sample.

The opening at the base of the cylindrical member (2) is then oriented upward, the fecal sampling part (12) of the fecal sampling stick (1) is then carefully inserted deeply, the male threading (14) of the fecal sampling stick (1) and the female threading (21) of the cylindrical member (2) are screwed together to advance the fecal sampling stick (1) forward, and the sealing film (25) of the cylindrical member (2) is penetrated by the fecal sampling stick (1) to wipe of the excess stool sample adhering to the fecal sampling part (12), allowing a certain amount of the fecal sample to be collected in the container body (3). At this time, the hole for adjusting the aspiration level is closed by the resistance during the penetration of the sealing film by the fecal sampling part, preventing stool from leaking out the hole for adjusting the aspiration level and allowing the necessary amount of stool to be dissolved in the stool-dissolving buffer.

The male threading (13) of the fecal sampling stick (1) and the female threading (21) of the cylindrical member (2) are screwed together (see FIG. 4) to ensure a liquid-tight seal between the outer wall of the fecal sampling stick (1) and the inner wall of the cylindrical member (2) to prevent leakage of the fecal sample that has been naturally dissolved and suspended in the stool-dissolving buffer in the interior (referred to below as analyte). In addition, at this time, the hole (122) for adjusting the aspiration level can also be positioned in advance to be more toward the distal end side from the sealing film (25) when the male threading (13) of the fecal sampling stick (1) and the female threading (21) of the cylindrical member (2) are screwed together, preventing the fecal sample from leaking. The cap (43) can be taken off the drip portion (33) to allow drops of analyte to be poured out the drip portion (33) for analysis.

Example 4

Another feces collection container of the invention will be described below with reference to drawings.

As illustrated in FIG. 16, the feces collection container of the invention comprises a fecal sampling stick (1), a cylindrical member (2), and a container body (3), wherein: the cylindrical member (2) is open at both ends so that the fecal sampling stick (1) is retractably inserted, the base of the container body (3) is sealed with a sealing film (31) that can be penetrated by the fecal sampling stick (1), and the tip is provided with a drip portion (33) that is sealed off by readily openable sealing means (4). The outer wall of the fecal sampling stick (1) and the inner wall of the cylindrical member (2) as well as the tip of the cylindrical member (2) and the base of the container body (3) are engaged in a liquid-tight manner, respectively.

The differences from the feces collection container illustrated in FIG. 12 are that the sealing membrane is provided in the container moan body (3), not the cylindrical member (2), and the cylindrical member (2) is integrally attachable and detachable with the fecal sampling stick (1), allowing the fecal sampling part (12) to be retractably operated.

When preparing the suspension, the cylindrical member (2) is first taken out of the container body (3). The seal or the like (not shown) securing the fecal sampling stick (1) is then taken out of the feces collection container, and the holding part (11) of the fecal sampling stick (1) is rotated to advance and expose the fecal sampling part (12). The fecal sampling part (12) is then brought down into contact with the surface of the stool that is to be analyzed and scrape to collect the sample. When the stool is a liquid such as diarrhea or watery stool, the fecal sampling part (12) is brought down and stirred in the liquid while the aspiration hole (121) is submerged below the surface of the stool liquid to collect the sample. The male threading (13) of the fecal sampling stick (1) is detached from the female threading (21) of the cylindrical member (2) to back off the fecal sampling stick (1), and the male threading

(14) and female threading (21) are screwed together, allowing the fecal sampling part (12) to be housed in the cylindrical member (2) as illustrated in FIG. 18. A ring-shaped protrusion (23) is provided on the inner wall on the base side from the position where the fecal sampling part (12) of the cylindrical member (2) is retracted, so that there is no risk of excess stool flowing to the base side of the cylindrical member (2).

Then, as shown in FIG. 16, the engagement part (22) of the cylindrical member (2) is engaged with the engagement part (32) of the container body (3) (resulting in liquid-tightness between the outer wall of the cylindrical member (2) and the inner wall of the container body (3)), the male threading (14) of the fecal sampling stick (1) and the female threading (21) of the cylindrical member (2) are then unscrewed to advance the fecal sampling stick (1) forward, and the sealing film (31) of the container body (3) is penetrated by the fecal sampling stick (1) to wipe of the excess stool sample adhering to the fecal sampling part (12), allowing a certain amount of the fecal sample to be collected in the container body (3). At this time, the hole for adjusting the aspiration level is closed by the resistance during the penetration of the sealing film by the fecal sampling part, preventing stool from leaking out the hole for adjusting the aspiration level and allowing the necessary amount of stool to be dissolved in the stool-dissolving buffer. The male threading (13) of the fecal sampling stick (1) and the female threading (21) of the cylindrical member (2) are screwed together (see FIG. 19) to ensure a liquid-tight seal between the outer wall of the fecal sampling stick (1) and the inner wall of the cylindrical member (2) to prevent leakage of the fecal sample that has been naturally dissolved and suspended in the stool-dissolving buffer in the interior (referred to below as analyte). In addition, at this time, the hole (122) for adjusting the aspiration level can also be positioned in advance to be more toward the distal end side from the sealing film (25) when the male threading (13) of the fecal sampling stick (1) and the female threading (21) of the cylindrical member (2) are screwed together, preventing the fecal sample from leaking. The thin film 41 of the drip portion (33) can be penetrated with a special spike (not shown) or the like to allow drops of analyte to be poured out the drip portion (33) for analysis.

Another example of the opening closing means is described below.

Figure 21:
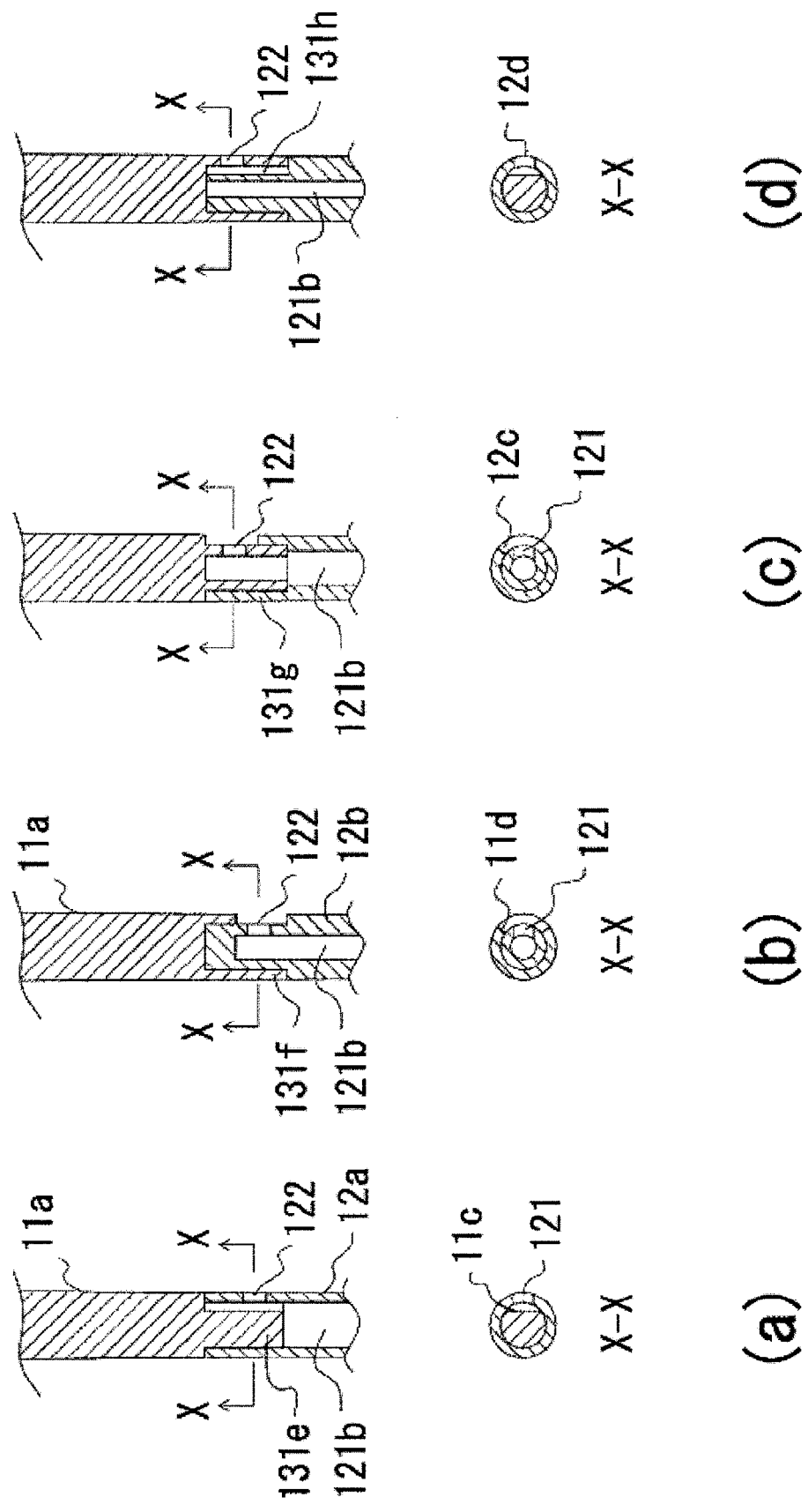
FIG. 21 is a cross section of another example of the opening sealing means in the feces collection container of the invention.

FIGS. 20 and 21 are cross sectional illustrations of another example of the opening closing means.

FIGS. 20(a) through (d) are of examples in which the base of the fecal sampling part side member (12a) and the tip of the holding part side member (11a) slide in a liquid-tight manner, and 131a, 131b, 131c, and 131d are opening closing means.

As illustrated in FIG. 20(a), the opening closing means is a protrusion (131a) in which the tip of the holding part side member (11a) has a smaller diameter than the other portion and is liquid-tightly inserted into the hollow (121b) of the fecal sampling part side member (12a). The hole (122) for adjusting the level of aspiration is provided in the base of the fecal sampling part side member (12a), and the protrusion (131a) relatively displaceably slides from the position where the hole (122) for adjusting the aspiration level is open to the position where it is closed.

As illustrated in FIG. 20(b), the opening closing means is a tip (131b) that is a hole inside the holding part side member (11a). The base of the fecal sampling part side member (12a) has a smaller diameter than the other portion, and is provided with the hole (122) for adjusting the aspiration level. The small diameter portion of the fecal sampling part member (12a) is liquid-tightly inserted into the hole of the tip of the holding part side member (11a). The tip (131b) which is the opening closing means relatively displaceably slides from the position where the hole (122) for adjusting the aspiration level is open to the position where it is closed.

As illustrated in FIG. 20(c), the opening closing means is a hole with a larger diameter than the hollow (121b) of the fecal sampling part side member (12a). The hole (122) for adjusting the aspiration level is provided in the tip of the holding part side member (11a) which has a smaller diameter than the other portion. The small diameter portion of the holding part side member (11a) is inserted in a liquid-tight manner into the hole of the fecal sampling part side member (12a). The tip (131c) which is the opening closing means relatively displaceably slides from the position where the hole (122) for adjusting the aspiration level is open to the position where it is closed.

As illustrated in FIG. 20(d), the opening closing means is the tip (131d) of the fecal sampling part side member (12a) which has a smaller diameter than the other portion. The hole (122) for adjusting the aspiration level is provided in the tip of the holding part side member (11a) serving as the inner hole. The small diameter part of the fecal sampling part side member (12a) is inserted in a liquid-tight manner into the holding part side member (11a). The tip (131d) serving as the opening closing means relatively displaceably slides from the position where the hole (122) for adjusting the aspiration level is open to the position where it is closed.

The examples in FIGS. 21(a) through (d) are examples in which the base of the fecal sampling part side member (12a) and the tip of the holding part side member (11a) are rotatably relatively displaceable in a liquid-tight manner.

As illustrated in FIG. 21(a), the opening closing means is a protrusion (131e) in which the tip of the holding part side member (11a) has a smaller diameter than the other portion, having been what is referred to as D cut, and is inserted in a liquid-tight manner into the hollow (121b) of the fecal sampling part side member (12a), and the fecal sampling part side member (12a) and holding part side member (11a) are rotatably relatively displaceable. The hole (122) for adjusting the aspiration level is provided in the base of the fecal sampling part side member (12a), and the protrusion (131a) relatively displaceably rotates from the position where the hole (122) for adjusting the aspiration level is open to the position where it is closed.

As illustrated in FIG. 20(b), the opening closing means is a tip (131f) that is a hole inside the holding part side member (11a), having a cut portion (11d). The base of the fecal sampling part side member (12a) has a smaller diameter than the other portion, and is provided with the hole (122) for adjusting the aspiration level. The small diameter portion of the fecal sampling part side member (12a) is liquid-tightly inserted into the hole of the tip of the holding part side member (11a), and the fecal sampling part side member (12a) and holding part side member (11a) are rotatably displaceable. The tip (131f) which is the opening closing means relatively displaceably rotates from the position where the hole (122) for adjusting the aspiration level is open to the position where it is closed.

As illustrated in FIG. 20(c), the opening closing means is a tip (131g) that is a hole with a larger diameter than the hollow (121b) of the fecal sampling part side member (12a), having a cut portion (12c). The hole (122) for adjusting the aspiration level is provided in the tip of the holding part side member (11a) which has a smaller diameter than the other portion. The small diameter portion of the holding part side member (11a) is inserted in a liquid-tight manner into the hole of the fecal sampling part side member (12a), and the fecal sampling part side member (12a) and holding part side member (11a) are rotatably relatively displaceable. The tip (131g) which is the opening closing means relatively displaceably rotates from the position where the hole (122) for adjusting the aspiration level is open to the position where it is closed.

As illustrated in FIG. 20(d), the opening closing means is the tip (131h) of the fecal sampling part side member (12a) which has a smaller diameter than the other portion, having been D cut. The hole (122) for adjusting the aspiration level is provided in the tip of the holding part side member (11a) serving as the inner hole. The small diameter part of the fecal sampling part side member (12a) is inserted in a liquid-tight manner into the holding part side member (11a), and the fecal sampling part side member (12a) and holding part side member (11a) are rotatably relatively displaceable. The tip (131h) serving as the opening closing means relatively displaceably slides from the position where the hole (122) for adjusting the aspiration level is open to the position where it is closed.

The examples above are examples in which the base of the fecal sampling part side member (12a) and the tip of the holding part side member (11a) can slide or rotate relatively displaceable, but can, so-called, spiral-displace which can compositely slide and rotate relatively displaceable.

The invention claimed is:

1. A feces collection container for collecting feces as an analyte comprising
   a fecal sampling stick which has a holding part at a base, a fecal sampling part at a tip and is formed a hollow passage with a tip opening and a base side opening on the base side a predetermined distance from the tip, and
   an opening closing means which is closable to the base side opening in a liquid-tight manner.

2. The feces collection container according to claim 1, wherein the fecal sampling stick is composed of a fecal sampling part side member and a holding part side member which are relatively displaceably connected,
   one of the fecal sampling part side member and the holding part side member has the base side opening, and the other that is relatively displaced from the position where the base side opening is open to the position where it is closed has the opening closing means.

3. The feces collection container according to claim 2, wherein the fecal sampling part side member has the base side opening, and the tip of the holding part side member is the opening closing means.

4. The feces collection container according to claim 2, wherein the holding part side member has the base side opening, and the base of the fecal sampling part side member is the opening closing means.

5. The feces collection container according to claim 2, wherein the fecal sampling part side member and the holding part side member is slidably relatively displaceable.

6. The feces collection container according to claim 2, wherein the fecal sampling part side member and the holding part side member is rotatably relatively displaceable.

7. The feces collection container according to claim 1, comprising
   the fecal sampling stick,
   a cylindrical member being open at both ends so that the fecal sampling stick is retractably inserted, and
   a container body in which the tip is provided with a drip portion that is sealed off by readily openable sealing means,
   an outer wall of the fecal sampling stick and an inner wall of the cylindrical member are engaged in a liquid-tight manner, and
   the tip of the cylindrical member and the base of the container body are engaged in a liquid-tight manner.

8. The feces collection container according to claim 7, wherein the tip of the cylindrical member is sealed off by a sealing film that is penetratable by the fecal sampling stick.

9. The feces collection container according to claim 7, wherein the base of the container body is sealed off by a sealing film that is penetratable by the fecal sampling stick.

10. The feces collection container according to claim 7, wherein a tip of the fecal sampling stick has a protrusion for penetrating the sealing film.

11. The feces collection container according to claim 7, wherein the sealing means of the drip portion is a thin film that is easily breakable.

12. The feces collection container according to claim 7, wherein the sealing means of the drip portion is a seal that is easily breakable at a fragile part.

13. The feces collection container according to claim 7, wherein the sealing means of the drip portion is a cap.

14. The feces collection container according to claim 1, wherein the opening closing means relatively displaces from the position where the base side opening is open to the position where it is closed by the resistance during the penetration of the sealing film by the fecal sampling stick.

* * * * *